United States Patent
Heneghan et al.

(10) Patent No.: US 8,562,526 B2
(45) Date of Patent: Oct. 22, 2013

(54) APPARATUS, SYSTEM, AND METHOD FOR MONITORING PHYSIOLOGICAL SIGNS

(75) Inventors: Conor Heneghan, Dublin (IE); Conor Hanley, Dublin (IE); Niall Fox, Offaly (IE); Philip De Chazal, Monkstown (IE)

(73) Assignee: ResMed Sensor Technologies Limited (IE)

( * ) Notice: Subject to any disclaimer, the term of this patent is extended or adjusted under 35 U.S.C. 154(b) by 1248 days.

(21) Appl. No.: 12/302,704

(22) PCT Filed: Jun. 1, 2007

(86) PCT No.: PCT/US2007/070196
§ 371 (c)(1),
(2), (4) Date: Nov. 26, 2008

(87) PCT Pub. No.: WO2007/143535
PCT Pub. Date: Dec. 13, 2007

(65) Prior Publication Data
US 2009/0203972 A1  Aug. 13, 2009

Related U.S. Application Data

(60) Provisional application No. 60/803,657, filed on Jun. 1, 2006.

(51) Int. Cl.
*A61B 5/00*  (2006.01)
(52) U.S. Cl.
USPC .............................. 600/301; 702/19; 128/920
(58) Field of Classification Search
None
See application file for complete search history.

(56) References Cited

U.S. PATENT DOCUMENTS 2,634,413 A * 4/1953 Potter .......................... 342/104
3,796,208 A   3/1974 Bloice
(Continued)

FOREIGN PATENT DOCUMENTS

JP   2000-083927     3/2000
JP   2004252770 A    9/2004
(Continued)

OTHER PUBLICATIONS

"The Fundamentals of FFT-Based Signal Analysis and Measurement in LabVIEW and LabWindows/CVI" National Instruments. Published Jun. 8, 2009. 12 pages. Accessed Jan. 26, 2012. URL: http://zone.ni.com/deyzone/cda/tut/p/id/4278#toc0.*

(Continued)

*Primary Examiner* — Bill Thomson
*Assistant Examiner* — Davin K Sands
(74) *Attorney, Agent, or Firm* — Lerner, David, Littenberg, Krumholz & Mentlik, LLP

(57) ABSTRACT

An apparatus, system, and method monitors the motion, breathing, heart rate and sleep state of subjects, e.g., humans, in a convenient, non-invasive/non-contact, and low-cost fashion. More particularly, the motion, breathing, and heart rate signals are obtained through processing applied to a raw signal obtained in a non-contact fashion, typically using a radio-frequency sensor. Periods of sleep disturbed respiration, or central apnea can be detected through analysis of the respiratory signal. The mean heart rate, and derived information, such as the presence of cardiac arrhythmias can be determined from the cardiac signal. Motion estimates can be used to recognize disturbed sleep and periodic limb movements. The sleep state may be determined by applying a classifier model to the resulting streams of respiratory, cardiac and motion data. A means for display of the sleep state, respiratory, cardiac, and movement status may also be provided.

33 Claims, 14 Drawing Sheets

(56) References Cited

U.S. PATENT DOCUMENTS

| | | | |
|---|---|---|---|
| 3,911,899 A | | 10/1975 | Hattes |
| 3,993,995 A | | 11/1976 | Kaplan et al. |
| 4,085,740 A | | 4/1978 | Allen, Jr. |
| 4,513,748 A | | 4/1985 | Nowogrodzki et al. |
| 4,958,638 A | * | 9/1990 | Sharpe et al. ............... 600/407 |
| 5,314,037 A | * | 5/1994 | Shaw et al. ................. 180/169 |
| 5,361,070 A | | 11/1994 | McEwan |
| 5,549,113 A | | 8/1996 | Halleck et al. |
| 5,573,012 A | | 11/1996 | McEwan |
| 5,590,650 A | | 1/1997 | Genova |
| 5,671,733 A | * | 9/1997 | Raviv et al. ................. 600/301 |
| 5,766,208 A | | 6/1998 | McEwan |
| 5,902,250 A | * | 5/1999 | Verrier et al. ............... 600/515 |
| 5,966,090 A | | 10/1999 | McEwan |
| 6,011,477 A | | 1/2000 | Teodorescu et al. |
| 6,062,216 A | | 5/2000 | Corn |
| 6,132,371 A | | 10/2000 | Dempsey et al. |
| 6,146,332 A | | 11/2000 | Pinsonneault et al. |
| 6,359,597 B2 | | 3/2002 | Haj-Yousef |
| 6,492,933 B1 | * | 12/2002 | McEwan ...................... 342/28 |
| 6,834,251 B1 | | 12/2004 | Fletcher |
| 6,839,581 B1 | * | 1/2005 | El-Solh et al. ............... 600/324 |
| 6,932,769 B2 | | 8/2005 | Griffin et al. |
| 7,196,629 B2 | | 3/2007 | Ruoss et al. |
| 7,199,749 B2 | | 4/2007 | Greneker, III et al. |
| 7,272,431 B2 | | 9/2007 | McGrath |
| 7,387,607 B2 | | 6/2008 | Holt et al. |
| 7,428,468 B2 | | 9/2008 | Takemura et al. |
| 7,468,034 B2 | | 12/2008 | Ouchi |
| 7,473,228 B2 | | 1/2009 | Griffin et al. |
| 2003/0092975 A1 | | 5/2003 | Casscells, III et al. |
| 2003/0201894 A1 | * | 10/2003 | Li ............................... 340/573.1 |
| 2004/0073098 A1 | * | 4/2004 | Geva et al. ................... 600/300 |
| 2004/0249258 A1 | * | 12/2004 | Tupin et al. .................. 600/407 |
| 2004/0249296 A1 | | 12/2004 | Ellscheid et al. |
| 2005/0043645 A1 | * | 2/2005 | Ono et al. .................... 600/529 |
| 2005/0073424 A1 | | 4/2005 | Ruoss et al. |
| 2005/0119532 A1 | | 6/2005 | Cloutier |
| 2005/0119711 A1 | * | 6/2005 | Cho et al. ..................... 607/42 |
| 2005/0128124 A1 | | 6/2005 | Greneker et al. |
| 2005/0240087 A1 | | 10/2005 | Keenan et al. |
| 2006/0079164 A1 | | 4/2006 | DeCastro et al. |
| 2006/0111635 A1 | | 5/2006 | Todros et al. |
| 2006/0189924 A1 | | 8/2006 | Blakley et al. |
| 2006/0241510 A1 | | 10/2006 | Halperin et al. |
| 2006/0270941 A1 | | 11/2006 | Xie et al. |
| 2007/0027367 A1 | | 2/2007 | Oliver et al. |
| 2008/0157956 A1 | | 7/2008 | Radivojevic et al. |
| 2008/0234568 A1 | | 9/2008 | Ouchi |
| 2008/0238757 A1 | * | 10/2008 | Lin et al. ...................... 342/22 |
| 2008/0269589 A1 | | 10/2008 | Thijs et al. |
| 2009/0256739 A1 | * | 10/2009 | Teshirogi et al. ............. 342/204 |

FOREIGN PATENT DOCUMENTS

| | | |
|---|---|---|
| JP | 2005270570 A | 10/2005 |
| WO | 2004/114193 | 12/2004 |

OTHER PUBLICATIONS

European Search Report and Search Opinion for European Patent Application No. 07784266.4, mailed Oct. 7, 2010.
Droitcour et al., Range Correlation and I/Q Performance Benefits in Single-Chip Silicon Doppler Radars for Noncontact Cardiopulmonary Monitoring, IEEE Transactions on Microwave Theory and Techniques, Mar. 3, 2004, vol. 52, No. 3, pp. 838-848.
International Search Report PCT/US07/070196 dated Feb. 22, 2008.
Second Office Action dated Apr. 14, 2011 of Chinese Appl. No. 200780026740.0 filed Jan. 14, 2009 (16 pages).
International Search Report and Written Opinion of the International Searching Authority for PCT International Application No. PCT/US2007/083155, mailed Mar. 20, 2008.
Written Opinion of the International Searching Authority for PCT International Application No. PCT/US2007/070196, mailed Feb. 22, 2008.
International Preliminary Report on Patentability for PCT International Application No. PCT/US2007/070196, mailed Dec. 3, 2008.
Japanese Office Action dated Oct. 18, 2011 of Japanese Appl. No. 2009-513469 filed Jan. 30, 2009 (4 pages).
Japanese Office Action for Application No. 2009-513469 dated May 1, 2012.
Australian Examination Report for Application No. 2007256872 dated Mar. 20, 2012.
Japanese Office Action for Application No. 2009-513469 dated Nov. 27, 2012.

* cited by examiner

1310: Subject
1320: Transceiver
1330: Data logger
1340: Processor
1350: Visual display
1360: Audible means
1370: Auxiliary sensor (e.g., temperature, light, relative humidity)
1380: Auxiliary sensor (e.g., sound)

APPARATUS, SYSTEM, AND METHOD FOR MONITORING PHYSIOLOGICAL SIGNS

CROSS-REFERENCE TO RELATED APPLICATIONS

This application is a U.S. National Phase of PCT/US2007/070196, filed Jun. 1, 2007, and claims priority under the Paris Convention to U.S. Provisional Application Ser. No. 60/803,657 filed on Jun. 1, 2006, the entire contents of which are incorporated herein by reference.

BACKGROUND

This disclosure relates to the monitoring of motion, breathing, heart rate and sleep state of humans in a convenient and low-cost fashion, and more particularly to an apparatus, system, and method for acquiring, processing and displaying the corresponding information in a easily understandable format.

Monitoring of sleep patterns, heart rate and respiration during sleep is of interest for many reasons from clinical monitoring of obstructive and central sleep apnea in both adults and young children, to ensuring healthy sleep patterns in young babies. For example, infants which are born prematurely often have immature cardiorespiratory control which can cause them to stop breathing for 15-20 seconds, or to breathe shallowly. This is referred to as apnea of prematurity, and often persists for two to three months after birth. Periodic breathing (in which the amplitude of respiration rises and falls over several minutes) is also common in babies born prematurely. In such infants, it is also useful to monitor heart rate as a low heart rate (bradycardia) can be used as a warning signal that the baby is not receiving sufficient oxygen.

In adults, common sleep disordered breathing syndromes include obstructive sleep apnea and central sleep apnea. In obstructive sleep apnea, the upper airway collapses, restricting the flow of air to the lungs, even in the presence of ongoing respiratory effort. Obstructive sleep apnea can also cause characteristic changes in heart rate, which may be detrimental to the subject. Obstructive sleep apnea has a high prevalence in the adult population, affecting about 2-4% of adults over the age of 40. Obstructive events lead to a reduced flow of air to the lungs, and subsequently a lowering of oxygen level in the blood. Central sleep apnea is less common than obstructive sleep apnea in adults, and is distinguished by a complete loss of respiratory effort, which leads to a loss of air to the lungs, and eventually a lowering of oxygen in the blood. In both central and obstructive sleep apnea, the body's natural defense mechanisms will be stimulated by the oxygen desaturation, and eventually increase respiratory effort sufficient to restore airflow. However, this is often accompanied by an arousal (which can be observed in the person's electroencephalogram) which either wakes the person up momentarily, or brings them into a lighter stage of sleep. In either event, the person's sleep is disrupted, and they experience poor quality sleep, which often leads to excessive daytime sleepiness.

Other common sleep disorders in adults, whose effects are not related to respiration are Periodic Limb Movements Disorder (PLMD) and Restless Legs Syndrome (RLS). In PLMD, a subject makes characteristic repetitive movements (usually of the leg) every 30-40 seconds, leading to sleep disruption due to frequent awakenings. In RLS, the subject has an overwhelming desire to move or flex their legs as they fall asleep, again leading to disrupted sleep patterns. Monitoring of these unusual body movements is important to confirming the diagnosis of these conditions and initiating treatment.

The most common adult sleep disorder is insomnia which is defined as a difficulty in initiating or maintaining sleep. Chronic insomnia is estimated to affect about 10% of the American population. However, at present full clinical evaluation of sleep patterns relies on electroencephalograph (EEG) monitoring, often requiring a hospital stay. There is a need for simpler methods of assessing sleep patterns for adults in the home environment. For example, evidence has shown that sleep deprivation adversely alters the balance of leptin and ghrelin, two hormones which are significantly involved with the body's appetite control system. Voluntary sleep deprivation over a period of time (due to lifestyle choice) has been correlated with increased Body-Mass-Index (an indicator of obesity). Hence, objective measurement and control of sleep patterns may play a role in weight management.

Moreover, sleep is of particular important to young children. Infants spend more time asleep than awake in their first three years, emphasizing its crucial importance in development. Sleep is important for physical recuperation, growth, maturing of the immune system, brain development, learning, and memory. Conversely, infants who do not receive sufficient sleep or who sleep poorly often display poor mood, as well as having an adverse effect on their parents' sleep patterns. Indeed it is estimated that 20-30% of children under the age of 3 years have common sleep problems such as frequent night-wakings, and difficulty falling asleep on their own. Studies have shown that parents can help their babies achieve good sleep patterns through a variety of behavioral approaches. A non-invasive safe sleep monitor can assist in adopting such behavioral approaches. Automated collection of sleep information can help parents in assuring their children are sleeping adequately. For example, a system which monitors night-time sleep and daytime naps can provide information in the form of a visual sleep log which can be stored and visualized over a period of time (e.g., using a world wide web interface on a personalized page). The sleep monitor can also track sleep fragmentation (e.g., frequent awakenings during night-time sleep), which is correlated with infant contentment. Finally, characteristic changes in breathing, heart rate, and movement may be associated with night-time urination and defecation in infants, and hence can be used to alert parents to change diapers.

In adults, measurements of heart rate and breathing rate during sleep can be used as clinical markers for continuous health monitoring. For example, elevated breathing rates can be linked to forms of respiratory distress or diseases such as chronic obstructive pulmonary disease which require increased respiratory effort. It has been shown in clinical studies that a particular type of breathing pattern, referred to as Cheyne-Stokes respiration or periodic breathing, is a marker for poor prognosis in people with heart disease. Simultaneous measurement of respiration and cardiac activity can also allow evaluation of a phenomenon called respiratory sinus arrhythmia (RSA) in which the heart rate speeds up and slows down in response to each breath. The amplitude of this coupling effect is typically stronger in young healthy people, and therefore can be used as another health marker. Heart rate changes during sleep can also provide useful clinical information—elevated heart rates can be an indicator of systemic activation of the sympathetic nervous system, which can be associated with sleep apnea or other conditions. Furthermore, a common clinical problem is to monitor response to treatments aimed at stabilizing heart rhythm. For example, a common cardiac arrhythmia is atrial fibrillation (AF), in which the upper chambers of the heart beat irregularly. Consequently the heart rate is irregular and elevated. Common treatments for AF include pharmacological and surgical approaches, and a goal of the doctor is to provide follow-up monitoring to look for a reoccurrence of the arrhythmia. Non-invasive low-cost monitoring of heart rate during sleep is a useful mechanism to provide doctors with a means of providing such monitoring follow-up for this condition, and other cardiac arrhythmias.

Accordingly, a method, system or apparatus which can reliably monitor sleep patterns, breathing and heart rate during sleep, and motion during sleep would have utility in a variety of settings.

A variety of techniques have been disclosed in the background art for addressing the need for respiratory, cardiac and sleep monitoring. Respiratory monitoring is currently carried out primarily in a hospital environment using a variety of approaches. A common method for measuring respiratory effort uses inductance plethysmography, in which a person wears a tightly fitting elastic band around their thorax, whose inductance changes as the person breathes in and out. This technique has become the most widely used respiration monitoring technique in sleep medicine. A severe limitation of the method from a convenience point of view is that the person has to wear a band, and remains connected to the associated electronic recording device via wires.

An alternative system for measuring respiratory effort is to use impedance pneumography, in which the impedance change of the thorax is measured. This technique is often used in clinical infant apnea monitors, which generate an alarm in a baby monitor when no breathing is detected. In order to detect the breathing signal, electrodes must be attached to a sleeping infant. More generally, there are a number of commercial products available which use impedance measurements across the baby's chest to detect central apnea (e.g., the AmiPlus Infant Apnea Monitor produced and marketed by CAS Medical Systems). The limitation of this technology is that it requires electrodes to be attached to the baby, has an active electrical component, and needs to be used with caution as the wires can cause strangulation if not properly fitted.

Heart rate during sleep can be measured using conventional surface electrocardiogram measurements (typically referred to as a Holter monitor), in which a person typically wears three or more electrodes. A limitation of this method is the need to wear electrodes and the associated electronic recording device. Heart rate fitness monitors record heart rate by also measuring surface electrocardiogram, typically using a wearable chest band which has integrated electrodes. Again, there is the need to wear the device and also the accompanying signal collector (typically a wrist watch style device). Heart rate during sleep can also be measured using pulse oximetry, in which a photoplethysmogram is collected at the finger or ear. There is a characteristic variation in the pulse photoplethysmogram signal which corresponds to each beat of the heart.

Integrated systems for collecting heart rate and respiration using combinations of the techniques discussed above for heart rate and respiratory effort have been developed. In one commercial product, contact ECG and inductance plethysmograph sensors have been embedded in a custom-designed jacket. The cost of providing such a wearable system is relatively high, and the system requires contact sensors.

One indicator of sleep status is the degree of motion while lying down. Motion during sleep can be detected by wrist-worn accelerometers, such as those commercially marketed by MiniMitter as "Actiwatch®". These use microelectronic accelerometers to record limb movement during sleep. A limitation of this technology is the requirement for the individual to wear a device, and the fact that it is not integrated with simultaneous breathing and cardiac monitoring, which limits the physiological usefulness of such measurements. Motion can also be detected using under-mattress piezoelectric sensors, which produce a voltage spike when pressure is applied to the mat, and hence can detect movement.

Various approaches to measuring heart rate, respiration, and motion in a non-contact fashion have been described. One approach is to use optical interferometry to provide a non-contact method for determining respiration, cardiac activity and motion. However, a limitation of their invention is that the optical signals are blocked by clothes or bedding materials. The processing required to obtain and differentiate breathing, cardiac and motion elements is unclear. A second approach is to use ultrasonic waves to detect motion. A limitation of this approach is that signal-to-noise ratio can be poor due to low reflection, and respiration, motion and cardiac signals can not be collected simultaneously. A further non-contact measurement technique for assessing bodily motion is to use continuous wave radar (using electromagnetic radiation in the radio frequency range) in detecting respiration and heartbeat.

Limitations of previous methods to obtain physiological data using these non-contact methods include various sensor limitations (e.g., obstruction by bed clothes, poor signal-to-noise ratios, or the need for too large an antenna). Furthermore, the background art does not provide methods for extracting useful "higher-level" physiological status, such as breathing rate, cardiac rhythm status, sleep state, respiratory distress, or evidence of sleep disturbed breathing. The current disclosure also possesses advantages related to the fact that it requires very low levels of transmitted radio-frequency power (e.g., less than 0 dBm), can be made in a small size (e.g., the sensor can be 5 cm×5 cm×5 cm or less in size), can be battery powered, and is safe for human use.

SUMMARY

This disclosure provides various embodiments of an apparatus, system, and method for monitoring of motion, breathing, heart rate and sleep state of humans in a convenient and low-cost fashion. In various embodiments, a sensor unit suitable for being placed close to where the subject is sleeping (e.g., on a bedside table) may be interfaced with a monitoring and display unit where results can be analyzed, visualized and communicated to the user. The sensor unit and the display/monitoring unit can be incorporated into a single stand-alone unit, if desired. The unit may include one or more of a non-contact motion sensor (for detection of general bodily movement, respiration, and heart rate); a processing capability (to derive parameters such as sleep state, breathing rate, heart rate, and movement); a display capability (to provide visual feedback); an auditory capability (to provide acoustic feedback, e.g., a tone whose frequency varies with breathing, or an alarm which sounds when no motion is detected); a communications capability (wired or wireless) to transmit acquired data to a separate unit. This separate unit can carry out the processing, display and auditory capability mentioned above, and can also be a data logger.

In one embodiment, an apparatus useful in detecting, analyzing, and displaying one or more of respiration, cardiac activity, and bodily function or movement of a subject, may include a processor configured to analyze a signal reflected from the subject without physical contact with the subject and to derive measurements of said one or more of respiration, cardiac activity, and bodily function or movement therefrom; and a display configured to provide the analyzed and derived measurements to a local or remote user of the apparatus.

In another embodiment, a system for measuring, analyzing, and displaying one or more of a respiration parameter, cardiac activity, and bodily movement or function of a subject may include a transmitter arrangement configured to propagate a radio frequency signal toward the subject; a receiver arranged to receive a radio-frequency signal reflected from the subject; a processor arranged to analyze the reflected signal to produce measurements of one or more of a respiration parameter, cardiac activity, and a bodily movement or function, and a monitor to provide selected information to a local or remote user of the system by either an audible or visual indication, or both.

In another embodiment, a method for measuring, analyzing, and displaying one or more physiological parameters of a subject may include the steps of sensing a signal reflected from the subject; processing and analyzing the reflected signal; deriving said one or more physiological parameters pertaining to said subject, said one or more physiological parameters comprising one or more of a respiration parameter, cardiac activity, and bodily movement or function of a subject; and making selected derived information available to a user.

Additional sensing capabilities may be added to the sensor unit, including a sound sensor; a sensor for measuring body temperature from a distance (infrared); and sensors for environment humidity, temperature and light level.

The processing capability extracts information relating specifically to the separate breathing, heart rate, and motion components, and uses this raw information to derive higher level information such as sleep state, presence of sleep disordered breathing, cardiac arrhythmias, and sleep disturbance. The display capability provides a means for clearly communicating this physiological information in a clearly understandable fashion, such as providing a simple color indicator to indicate sleep status (awake or asleep). The processing capability can also incorporate measurements from the auxiliary sensors, which allows the derivation of physiological information about coughing, wheezing, and other respiratory disturbances.

BRIEF DESCRIPTION OF THE DRAWINGS

Embodiments of the disclosure will now be described with reference to the accompanying drawings in which.

DETAILED DESCRIPTION

Figure 1:
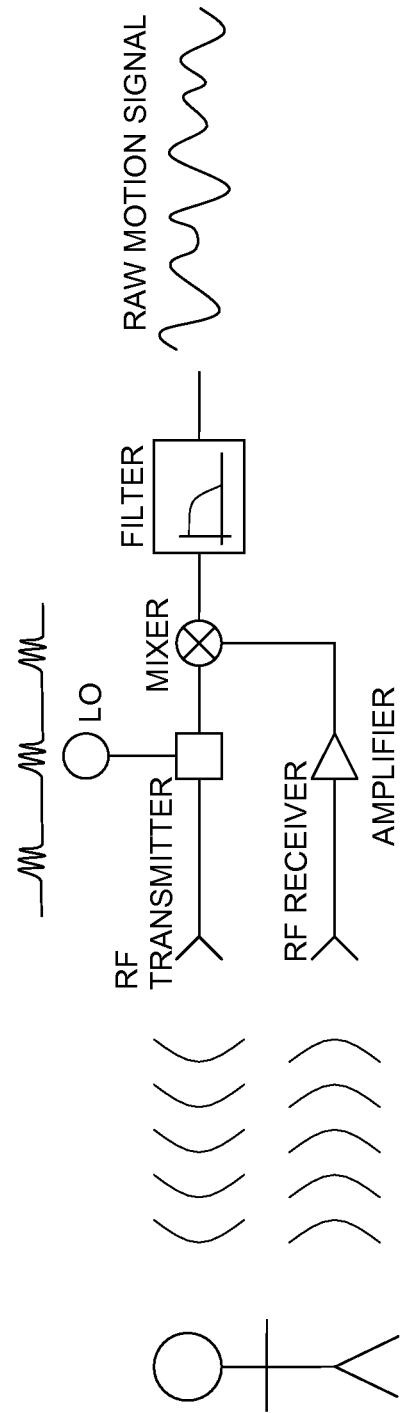
FIG. 1 is a diagram illustrating a schematic of the radio frequency sensor components of the system, with a pulsed continuous wave signal for illustration.

FIG. 1 is a diagram illustrating a schematic of the radio frequency sensor components of the apparatus and system, with a pulsed continuous wave signal for illustration. The transmitter transmits a radio-frequency signal towards a subject, e.g., a human. The reflected signal is then received, amplified and mixed with a portion of the original signal, and the output of this mixer is then low pass filtered. The resulting signal contains information about the movement, respiration and cardiac activity of the person, and is referred to as the raw sensor signal. In an alternative embodiment, the system may also use quadrature transmission in which two carrier signals 90 degrees out of phase are used. In the limits that the pulse becomes very short in time, such a system can be characterized as an ultrawideband (UWB) radio-frequency sensor.

Figure 2:
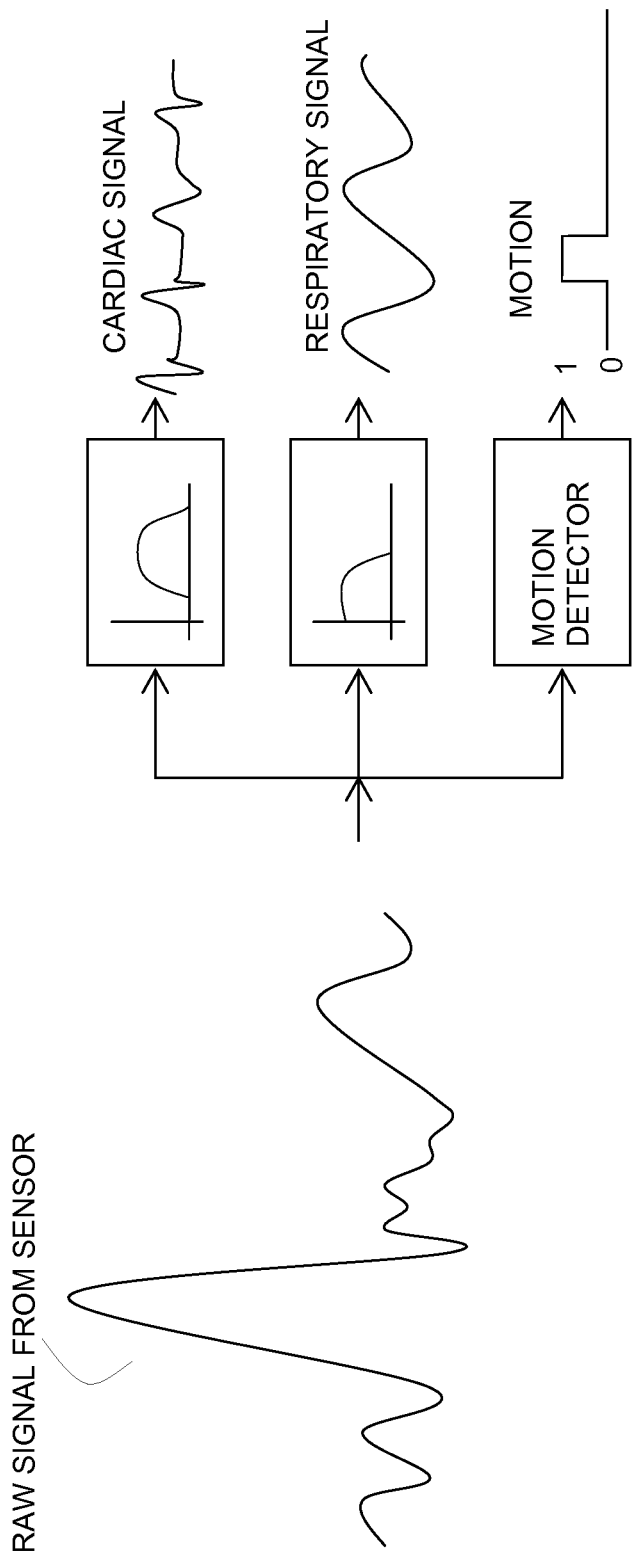
FIG. 2 is a diagram illustrating a schematic of how a raw sensor signal can be processed to produce three signals for further processing.

FIG. 2 is a diagram illustrating a schematic of how the raw sensor signal can be processed to produce three signals for further processing. The raw signal generally will contain components reflecting a combination of bodily movement, respiration, and cardiac activity. Bodily movement can be identified by using zero-crossing or energy envelope detection algorithms (or more complex algorithms), and used to form a "motion on" or "motion off" indicator. The respiratory activity is typically in the range 0.1 to 0.8 Hz, and can be derived by filtering the original signal with a bandpass filter whose passband is in that region. The cardiac activity is reflected in signals at higher frequencies, and this activity can be accessed by filtering with a bandpass filter with a pass band such as 1 to 10 Hz.

Figure 3:
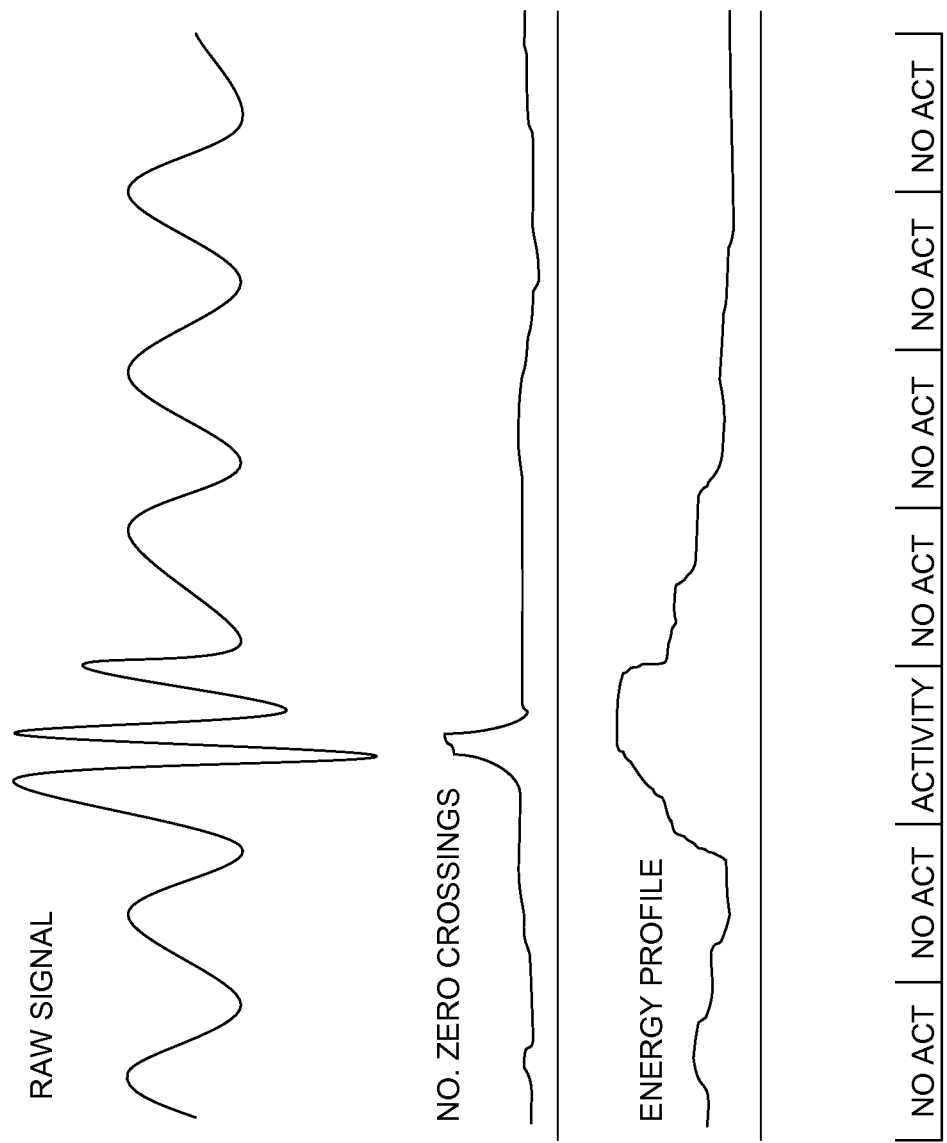
FIG. 3 is a diagram illustrating a more detailed view of a way by which the raw sensor signal can be processed to yield motion information.

FIG. 3 is a diagram illustrating a more detailed view of the means by which the raw sensor signal can be processed to yield motion information. One technique calculates the energy envelope of the signal over a period of time, and periods which have a high energy envelope by comparison with a threshold are determined to be periods of motion. A second technique counts the number of times the signal crosses a threshold (e.g., the zero value) and areas with a high value of zero-crossing are determined as being high motion areas. These techniques can be used separately or in combination to achieve a motion detection.

Figure 4:
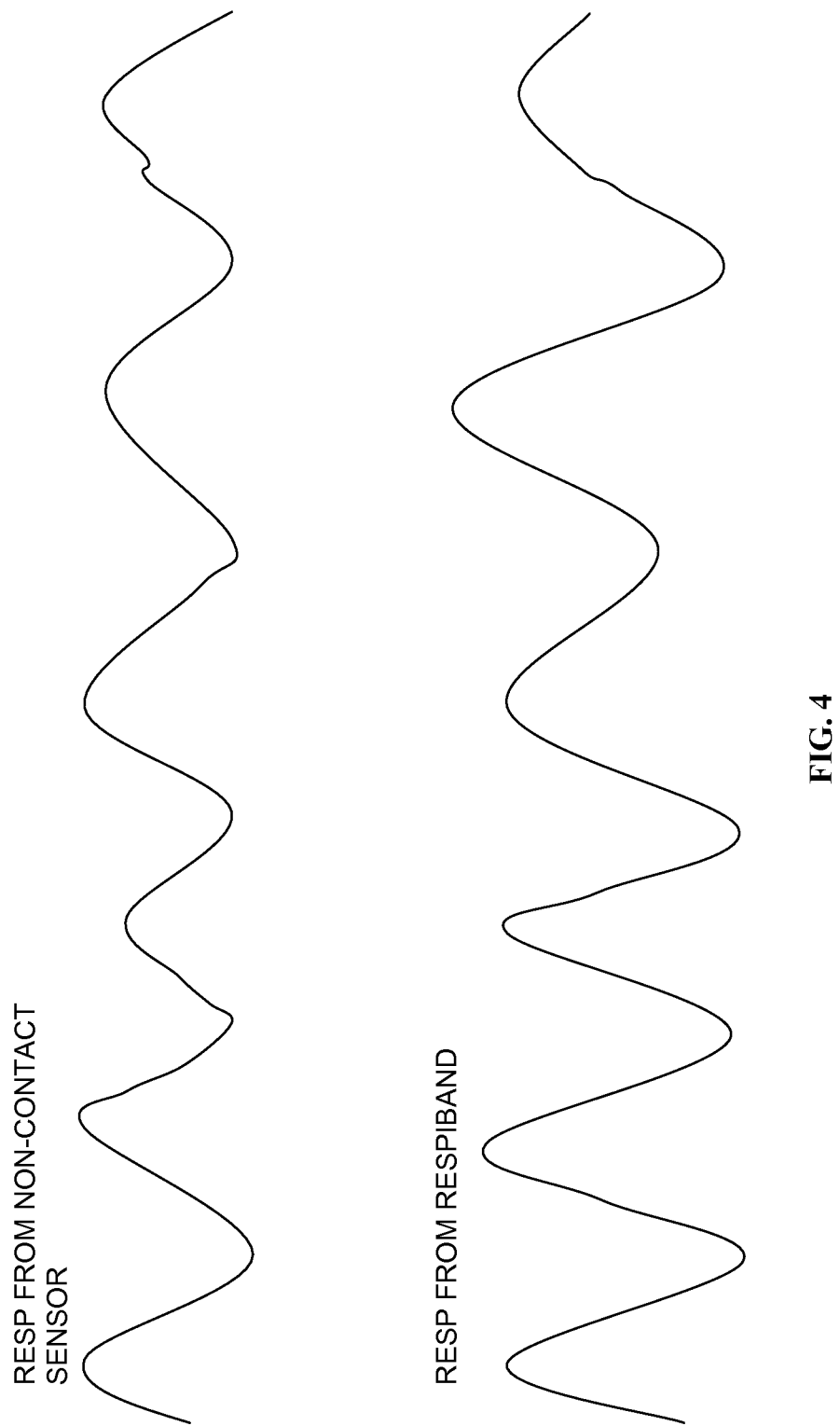
FIG. 4 is a diagram illustrating sample signals acquired from the system for respiratory activity, in comparison with the signals obtained from a conventional standard inductance plethysmography (using a commercial system called Respiband®)

FIG. 4 is a diagram illustrating sample signals acquired from the system for respiratory activity, in comparison with the signals obtained from the current clinical gold standard of inductance plethysmography (using a commercial system called Respiband®). The disclosed apparatus and system are capable of measuring both the amplitude and frequency of breathing.

Figure 5:
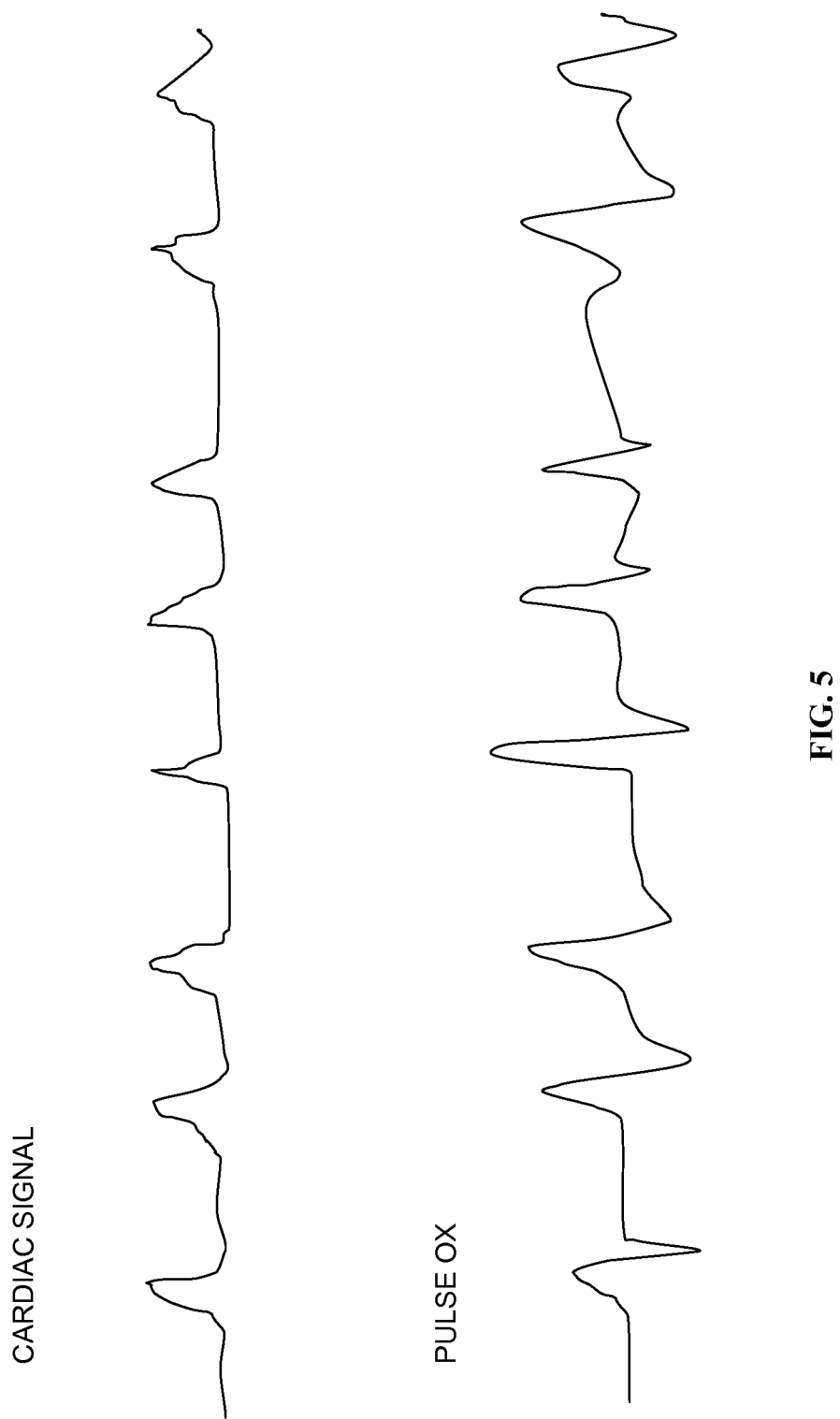
FIG. 5 is a diagram illustrating sample signals acquired from the system for cardiac activity in comparison with the signals obtained from an conventional heart rate monitoring system based on a pulse oximeter.

FIG. 5 is a diagram illustrating sample signals acquired from the apparatus and system for cardiac activity, in comparison with the signals obtained from a conventional heart rate monitoring system based on a pulse oximeter. The disclosed system is capable of acquiring signals in which individual heart beats can be distinguished.

Figure 6:
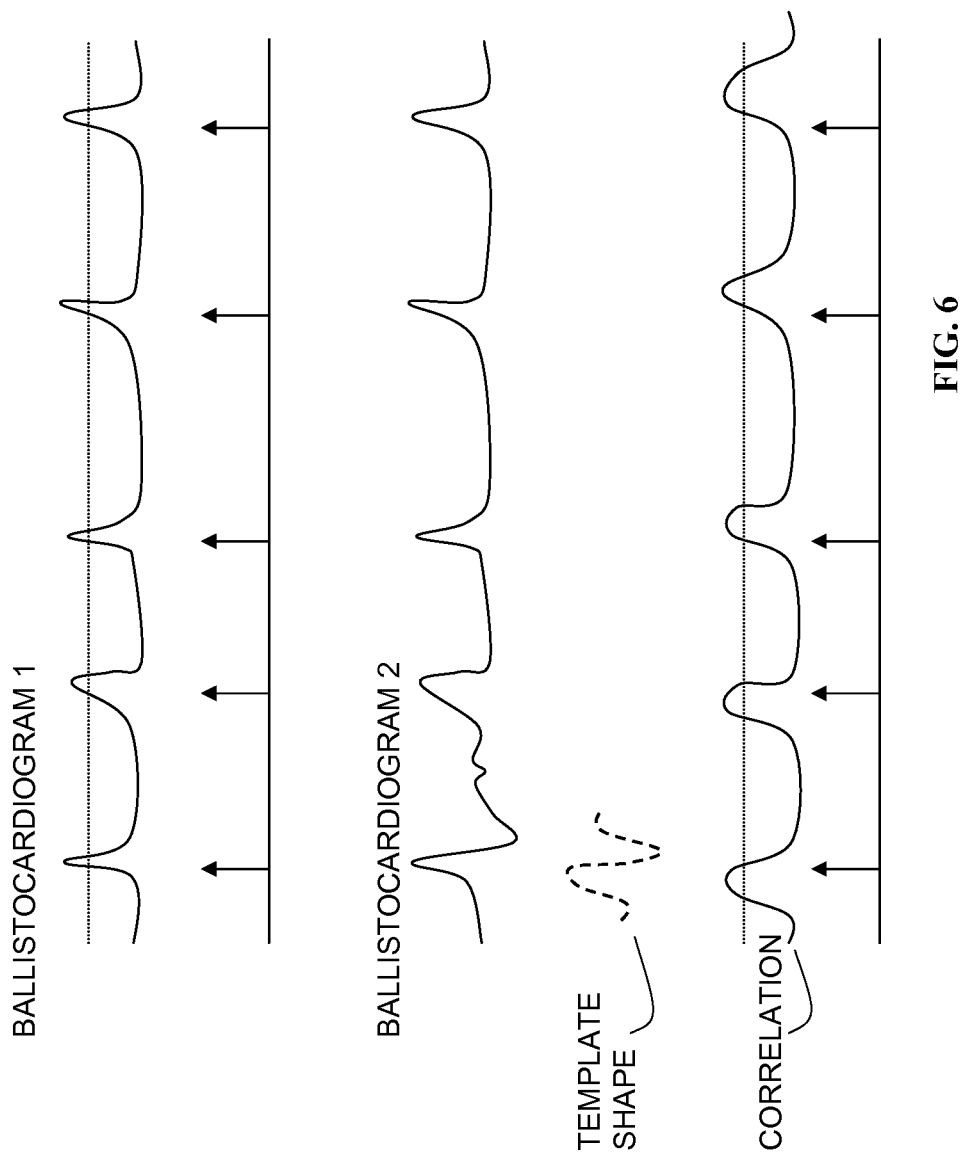
FIG. 6 is a diagram illustrating techniques by which the system may calculate heart rate.

FIG. 6 is a diagram illustrating techniques by which the apparatus and system may calculate heart rate. Cardiac activity causes a pressure wave at the surface of the body called the ballistocardiogram. In some cases (due to a combination of positioning, body type, and distance form the sensor), the cardiac signals will provide a signal in which individual pulses can be clearly seen. In such cases, heart beats will be determined by a threshold passing technique (a pulse is associated with the point where the signal exceeds the threshold). In more complex (but typical cases), the ballistocardiogram will present a more complex but repeatable pulse shape. Therefore a pulse shape template can be correlated with the acquired cardiac signal, and places where the correlation is high will be used as the heart beat locations.

Figure 7:
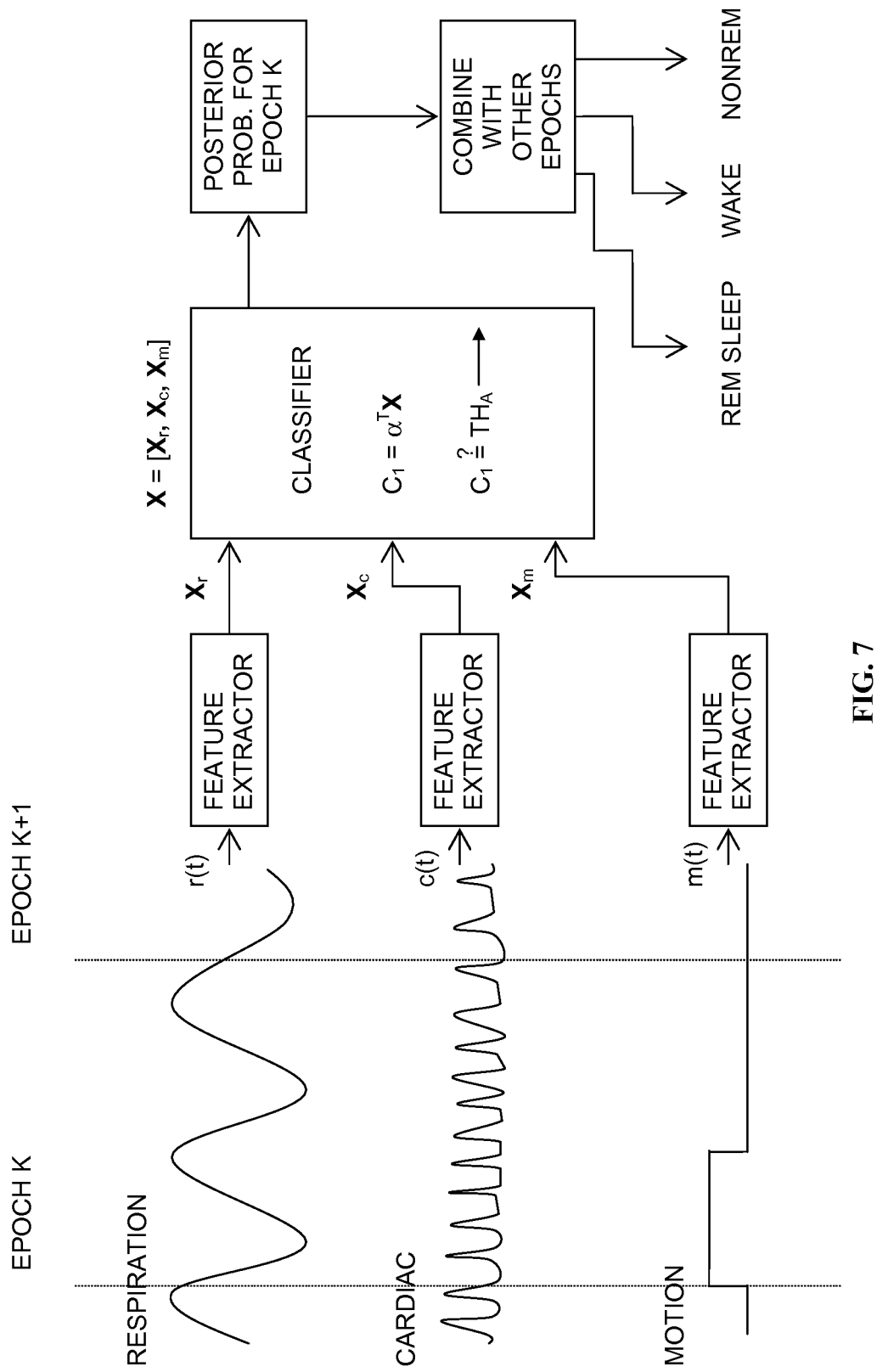
FIG. 7 is a diagram illustrating how information may be integrated from the derived motion m(t), respiratory r(t) and cardiac signals c(t) together to extract meaningful physiological classifications, by using a classifier model.

FIG. 7 is a diagram illustrating how the invention integrates information from the derived motion m(t), respiratory r(t) and cardiac signals c(t) together to extract meaningful physiological classifications, by using a classifier model. The three streams of data are segmented into time epochs, and statistical features are generated for each epoch. For example, these features might be the signal variance, spectral components, or peak values, and these are grouped into vectors Xr, Xn, and Xc. The vectors can then form a single vector X of features. These features are combined (for example in a linear weighted fashion using $\alpha^T X$) to determine the probability that the epoch corresponds to a certain physiological state (e.g., person asleep, person awake). The classification from epochs can be further combined with classification from other epochs to form higher level decisions (such as whether the person is in REM, NONREM, or WAKE states).

Figure 8:
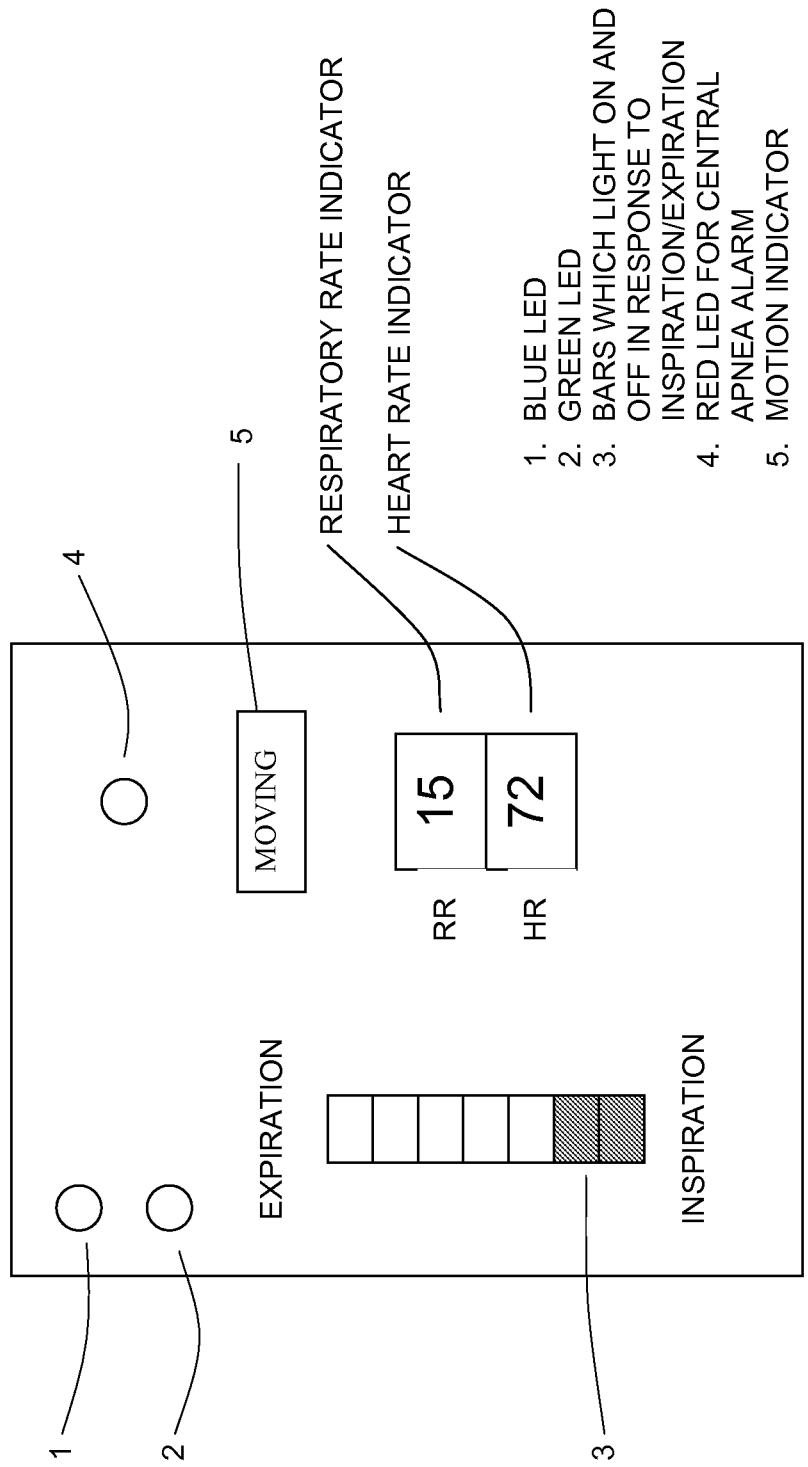
FIG. 8 is a diagram illustrating an example of an output displayed in one embodiment.

FIG. 8 is a diagram illustrating an example of outputs displayed in one embodiment. A light emitting diode may be used to indicate sleep state (awake or asleep) clearly to a user in the simplest case. The breathing of the subject may be graphically represented by a bank of lights which turn on and off as the person breathes in and out. For example, all of the lights will be off at the point of maximum inspiration, and all lights will be on at the point of maximum expiration. The display may also have a light emitting diode to indicate the central apnea alarm condition. The heart rate (beats per minute) and the breathing rate (breaths per minute) can be indicated in numerical or graphical format on the display. An indicator of whether the person is moving can also be included.

Figure 9:
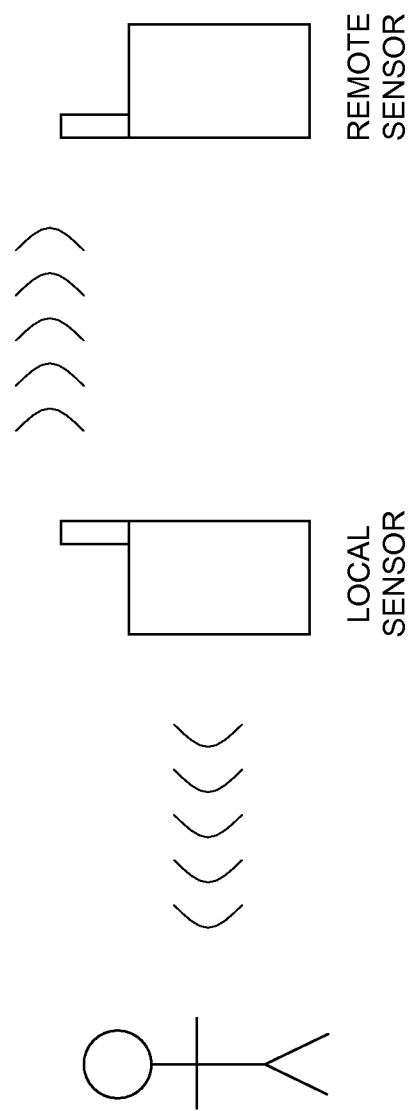
FIG. 9 is a diagram illustrating how the apparatus and system of this disclosure can be used in a wireless communications configuration where the processing and display unit are remote from the sensor unit.

FIG. 9 is a diagram illustrating how the apparatus and system of this disclosure can be used in a configuration where the processing and display unit is remote from the sensor unit, and communication between the two is achieved wirelessly.

Figure 10:
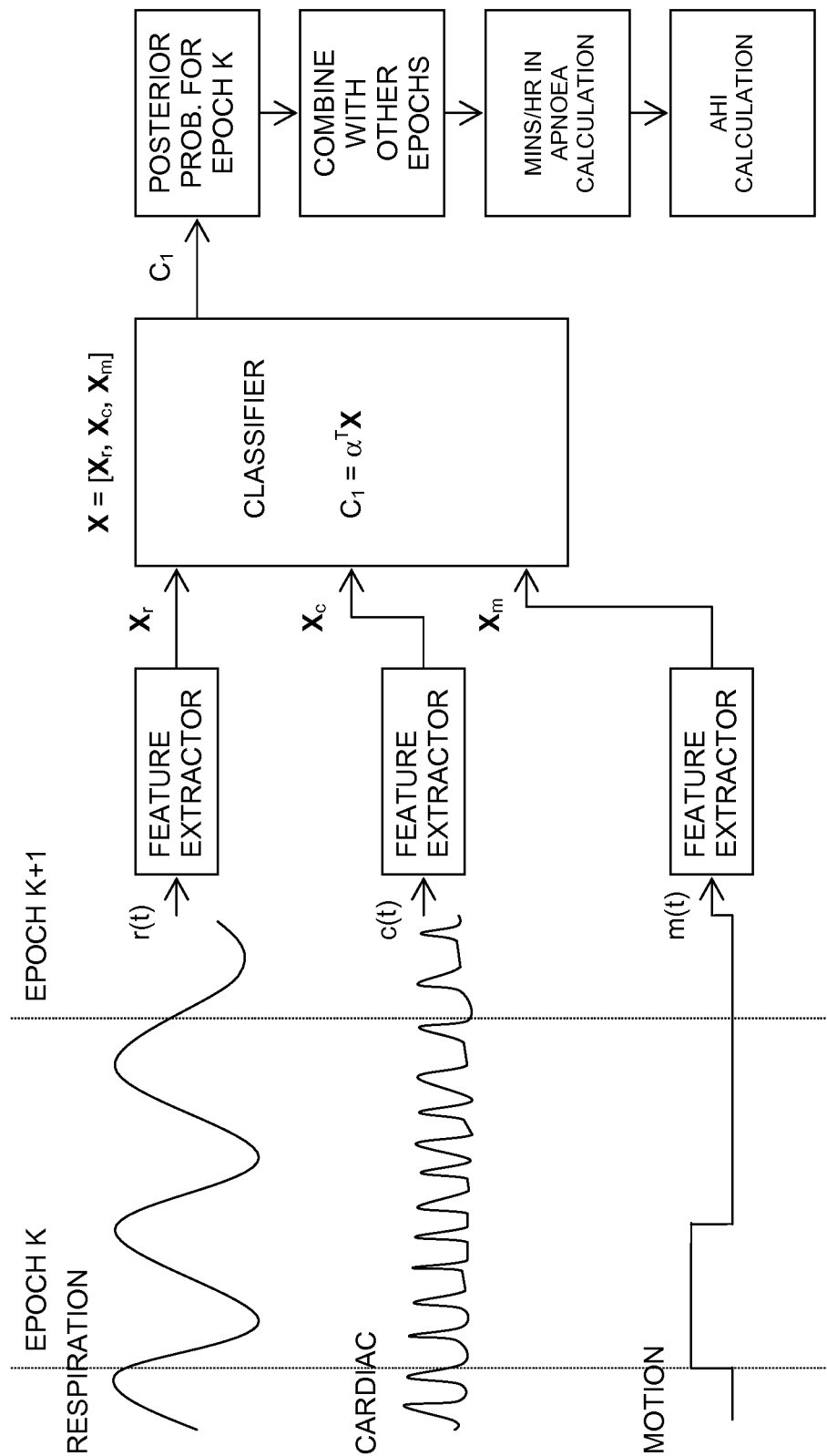
FIG. 10 is a diagram illustrating how information may be integrated from the derived motion m(t), respiratory r(t) and cardiac signals c(t) together to extract an Apnoea-Hypopnoea index (AHI) by using a classifier model.
Figure 11:
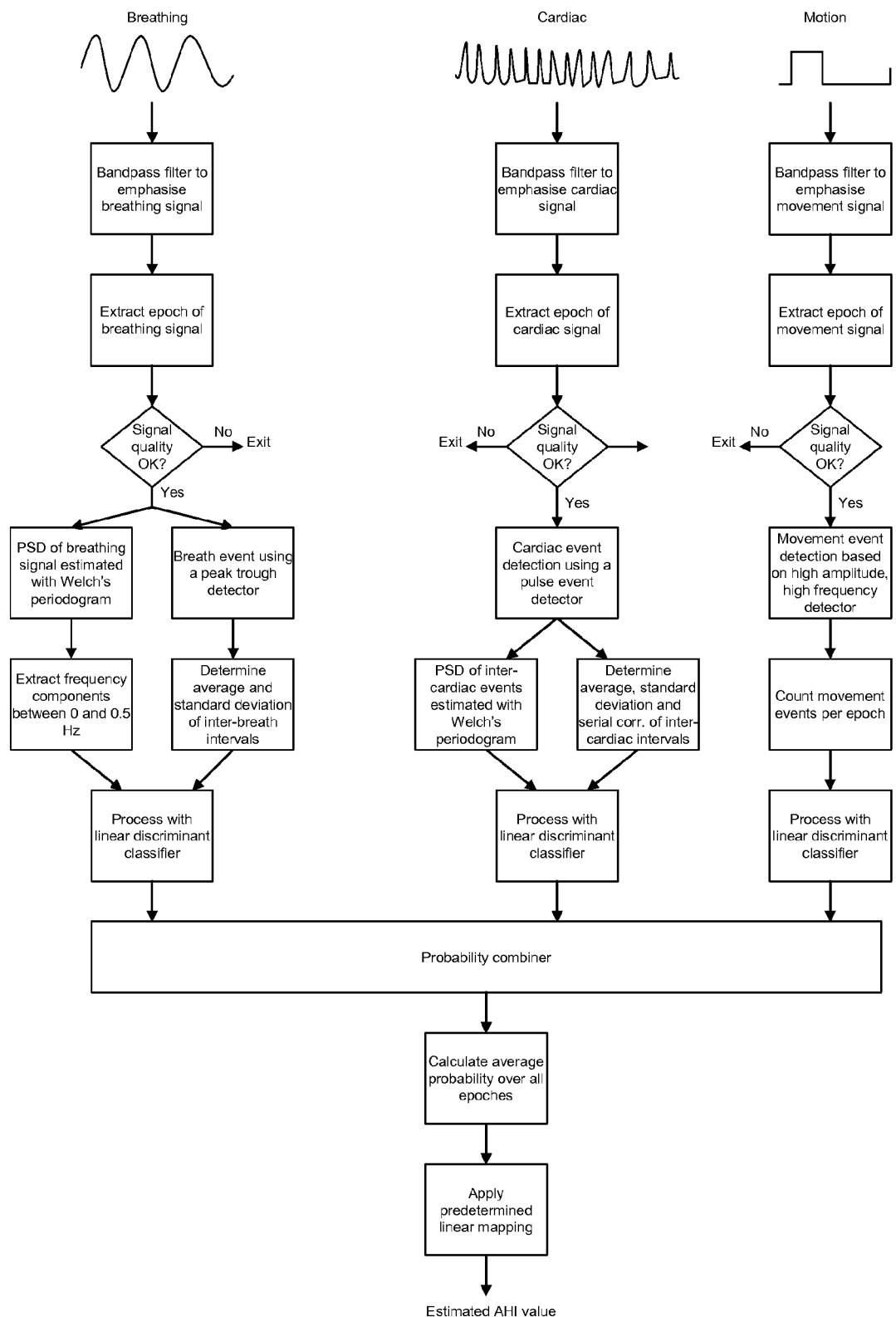
FIG. 11 is a diagram illustrating an algorithm for processing any combination of the breathing signal, heart-rate and movement signal to form an estimated AHI including using only measured and/or derived respiratory effort of a human subject.

FIG. 10 is a diagram illustrating how information may be integrated from the derived motion m(t), respiratory r(t) and cardiac signals c(t) together to extract an Apnoea-Hypopnoea index (AHI) by using a classifier model; an algorithm for processing any combination of the breathing signal, heart-rate and movement signal to form an estimated Apnoea-Hypopnoea index, and FIG. 11 is a diagram illustrating an algorithm for processing any combination of the breathing signal, heart-rate and movement signal to form an estimated AHI including using only measured and/or derived respiratory effort of a human subject.

Figure 12:
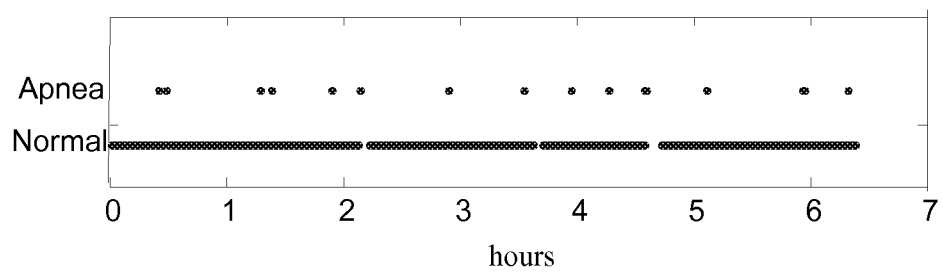
FIG. 12 illustrates an example output of the epoch labels of apnea estimated from the breathing signal from a night time recording of a subject for which the estimated AHI was 2.9 and the expert determined AHI was 4.

FIG. 12 illustrates an example output of the epoch labels of apnea estimated from the breathing signal from a night time recording of a subject for which the estimated AHI was 2.9 and the expert determined AHI was 4.

Figure 13:
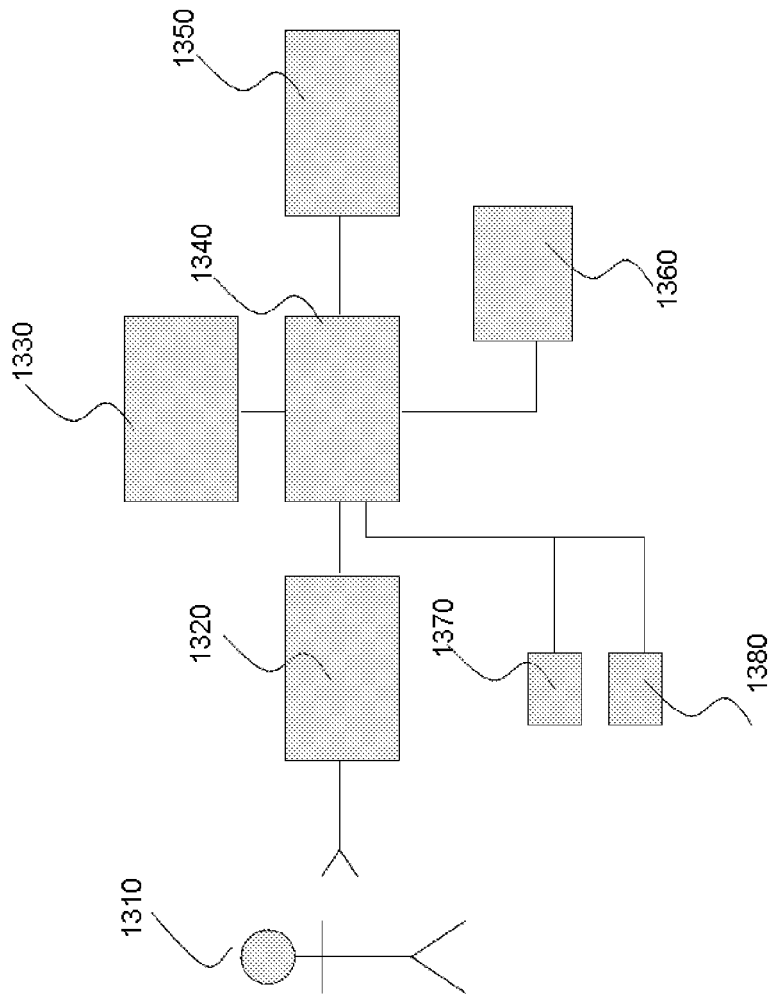
FIG. 13 is a block diagram of another embodiment of the apparatus and system of this disclosure illustrating auxiliary sensors.

FIG. 13 is a block diagram of another embodiment of the apparatus and system of this disclosure illustrating the possible use of auxiliary sensors such as sound, ultrasound, infrared, light, and/or relative humidity. It also demonstrates in block diagram format, a representative schematic of a specific embodiment which includes a transceiver, a processor, a data logger, a visual display means, an audible indicator, and auxiliary sensors.

In one embodiment, a system includes a sensor unit, which can be placed relatively close to where the subject is sleeping (e.g., on a bedside table) and a monitoring and display unit through which results can be analyzed, visualized and communicated to the user. The sensor unit and the display/monitoring unit may be incorporated into a single stand-alone unit, if required. The unit may contain one or more of the following features: a non-contact motion sensor for detection of general bodily movement, respiration, and heart rate; a processing capability to derive parameters such as sleep state, breathing rate, heart rate, and movement; a display capability to provide visual feedback; an auditory capability to provide acoustic feedback, e.g., a tone whose frequency varies with breathing, or an alarm which sounds when no motion is detected; and a wired or wireless communications capability to transmit acquired data to a separate unit. This separate unit can carry out the processing, display and auditory capability mentioned above.

Additional sensing capabilities can be added to the sensor unit, including a sound sensor; a sensor for measuring body temperature from a distance (infrared); and sensors for environment humidity, temperature and light level.

In one specific embodiment, the motion sensor may include a radio-frequency Doppler sensor, which can be used to transmit radio-frequency energy (typically in the range 100 MHz to 100 GHz), and which then uses the reflected received signal to construct a motion signal. The principle by which this works is that a radio-frequency wave $$s(t) = u(t)\cos(2\pi f_c t + \theta) \quad (1)$$

is transmitted from the unit. In this example, the carrier frequency is $f_c$, t is time, and θ is an arbitrary phase angle, and u(t) is a pulse shape. In a continuous wave system, the magnitude of u(t) is always one, and can be omitted from Eq. (1). More generally, the pulse will be defined as $$u(t) = \begin{cases} 1, t \in [kT \quad kT + T_p], k \in Z \\ 0 \end{cases} \quad (2)$$

where T is the period width, and $T_p$ is the pulse width. Where $T_p \ll T$, this becomes a pulsed continuous wave system. In the extreme case, as $T_p$ becomes very short in time, the spectrum of the emitted signal becomes very wide, and the system is referred to as an ultrawideband (UWB) radar or impulse radar. Alternatively, the carrier frequency of the RF transmitted signal can be varied (chirped) to produce a so-called frequency modulated continuous wave (FMCW) system.

This radio frequency signal may be generated by a transmitter collocated with the sensor using a local oscillator coupled with circuitry for applying the pulse gating or, with proper control of signal timing, the transmitter can separate from the receiver/sensor in a so-called "bistatic" configuration. In the FMCW case, a voltage controlled oscillator is used together with a voltage-frequency converter to produce the RF signal for transmission. The coupling of the RF signal to the air may be accomplished using an antenna. The antenna can be omnidirectional (transmitting power more-or-less equally in all directions) or directional (transmitting power preferentially in certain directions). It may be advantageous to use a directional antenna in this system so that transmitted and reflected energy is primarily coming from one direction. The apparatus, system, and method of this disclosure is compatible in various embodiments with various types of antenna such as simple dipole antennas, patch antennas, and helical antennas, and the choice of antenna can be influence by factors such as the required directionality, size, shape, or cost. It should be noted that the apparatus and system can be operated in a manner which has been shown to be safe for human use. The system has been demonstrated with a total system emitted average power of 1 mW (0 dBm) and lower. The recommended safety level for RF exposure is 1 mW/cm2. At a distance of 1 meter from a system transmitting at 0 dBm, the equivalent power density will be at least 100 times less than this recommended limit.

In all cases, the emitted signal will be reflected off objects that reflect radio waves (such as the air-body interface), and some of the reflected signal will be received at a receiver, which can be collocated with the transmitter, or which can be separate from the transmitter, in a so-called "bistatic" configuration. The received signal and the transmitted signal can be multiplied together in a standard electronic device called a mixer (either in an analog or digital fashion). For example, in the CW case, the mixed signal will equal $$m(t)=\gamma \cos(2\pi f_c t)\cos(2\pi f_c t+\phi(t)) \quad (3)$$

where $\phi(t)$ is the path difference of the transmitted and received signals (in the case where the reflection is dominated by a single reflective object), and $\gamma$ is the attenuation experienced by the reflected signal. If the reflecting object is fixed, then $\phi(t)$ is fixed, and so is m(t). In the case of interest to us, the reflecting object (e.g., chest) is moving, and m(t) will be time-varying. As a simple example, if the chest is undergoing a sinusoidal motion due to respiration:

$$resp(t)=\cos(2\pi f_m t) \quad (4)$$

then the mixed signal will contain a component at $f_m$ (as well as a component centred at $2f_c$ which can be simply removed by filtering). The signal at the output of the low pass filter after mixing is referred to as the raw sensor signal, and contains information about motion, breathing and cardiac activity.

The amplitude of the raw sensor signal is affected by the mean path distance of the reflected signal, leading to detection nulls and peaks in the sensor (areas where the sensor is less or more sensitive). This effect can be minimised by using quadrature techniques in which the transmitter simultaneously transmits a signal 90 degrees out of phase (the two signals will be referred to as the I and Q components). This will lead to two reflected signals, which can be mixed, leading eventually to two raw sensor signals. The information from these two signals can be combined by taking their modulus (or other techniques) to provide a single output raw sensor signal.

In the UWB case, an alternative method of acquitting a raw sensor signal may be beneficial. In the UWB case, the path distance to the most significant air-body interface can be determined by measuring the delay between the transmitted pulse and peak reflected signal. For example, if the pulse width is 1 ns, and the distance form the sensor to the body is 0.5 m, then the total time m(τ) elapsed before a peak reflection of the pulse will be 1/(3×108)s=3.33 ns. By transmitting large numbers of pulses (e.g., a 1 ns pulse every 1 μs) and assuming that the path distance is changing slowly, we can derive a raw sensor signal as the average of the time delays over that period of time.

In this way, the sensor, e.g., a radio-frequency sensor, can acquire the motion of the chest wall, or more generally the part of the body at which the system is aimed. Directional selectivity can be achieved using directional antennas, or multiple RF transmitters. A respiration signal acquired in this way using a pulsed continuous wave system is shown in the top panel of FIG. 4. We stress however that a continuous wave, an FMCW, or a UWB radar can also obtain similar signals.

Moreover, since the bulk of the reflected energy is received from the surface layer of the skin, this motion sensor can also obtain the ballistocardiogram, which is the manifestation of the beating of the heart at the surface of the skin due to changes in blood pressure with each beat. An example of a surface ballistocardiogram obtained with an RF motion sensor is shown in FIG. 5, together with a reference cardiogram signal from a finger-mounted pulse oximeter. In the received signal from a sleeping subject, the sensor will typically have a mixture of a respiration and a cardiac signal, as well as having motion artefacts. These various signals can be separated by signal processing using a variety of techniques including digital filtering techniques (e.g., a linear bandpass filter of bandwidth 2-10 Hz can be used to extract the cardiac signal primarily, while a bandpass filter of bandwidth 0.15 to 0.6 Hz can extract the respiration component). More general digital filtering techniques such as adaptive noise cancellation or non-linear filters may also be used. This is schematically illustrated in FIG. 2.

As mentioned above, the received signal can include large motion artifacts. This is due to the fact that the reflected signals from the body can contain more than one reflection path, and lead to complex signals (for example if one hand is moving towards the sensor, and the chest is moving away). Such a complex signal in response to upper body motion is shown in the raw signal illustrated in FIG. 2. The reception of such signals is useful as it can indicate that the upper body is in motion, which is useful in determining sleep state. The sensor can also be used to detect motion signals from the lower part of the body (such as involuntary leg jerks) which are useful in the diagnosis of sleep disorders such as Restless Legs Syndrome or Periodic Limb Movements.

In order to improve the qualities of the measured respiration, cardiac, and motion signals, the physical volume from which reflected energy is collected by the sensor can be restricted using various methods. For example, the transmission antenna can be made "directional" (that is, it transmits more energy in certain directions), as can the receiver antenna. A technique called "time-domain gating" can be used to only measure reflected signals which arise from signals at a certain physical distance form the sensor. Frequency domain gating can be used to restrict motions of the reflected object above a certain frequency.

In a simple embodiment of the system, a single antenna will be used, with a single carrier frequency. This antenna will act as both the transmit and receive antenna. However, in principle, multiple receive and transmit antennas can be used, as can multiple carrier frequencies. In the case of measurements at multiple frequencies (e.g., at 500 MHz and 5 GHz) the lower frequency can be used to determine large motions accurately without phase ambiguity, which can then be subtracted from the higher-frequency sensor signals (which are more suited to measuring small motion). Using this sensor, the system collects information from the person, and uses that to determine breathing, heart rate, and motion information.

The additional optional sensors can be incorporated as follows. The optional acoustic sensor in the monitoring is a microphone responsive to sound energy in the range 20-10 KHz (for example), and can be used to determine background noises, and noises associated with sleeping (e.g. snoring). Background noise cancellation techniques can be used to emphasise the person's breathing noise, if necessary. The subject's surface temperature can be measured using an infrared device. Other environmental parameters can be collected such as temperature, humidity and light level using known sensor technology. In particular, motion activity can also be collected from an under-mattress piezoelectric sensor, and this motion signal can then be used as a substitute or to complement the motion signal obtained from the radio-frequency sensor.

All of these sensor inputs may be fed into the unit for processing and display purposes, and for possible transmission to a separate unit (the monitoring unit).

The system can then use its processing capability to combine the sensor inputs to provide a number of useful outputs, and to display these outputs in a meaningful manner. These steps are carried out in the following manner.

Information about bodily motion is determined in the following way. If the person moves, there will be a corresponding large change in the received signal from the non-contact sensor, due to the sudden significant change in the radio-frequency path length. These "motion events" can be recognised by comparing the energy of the signal over a short epoch (typically 0.5 to 5 seconds) with the baseline movement seen by the sensor over a longer period of time (refer to FIG. 3). If the energy in the epoch exceeds a predetermined threshold relative to the proceeding time, then that epoch is judged to be an "activity event" and is marked as such. The amount by which the energy exceeds the threshold can be used to weight the amplitude of the activity of the event. Alternatively, motion can be detected by counting "threshold-crossings"— the number of times the signal passes through a preset level. This is also called a zero-crossing technique.

In that way, a motion profile can be built up of the received signal. By comparison with a database of previously collected motion profiles, the overall motion can be classified into categories such as "no motion", "slight motion" or "large motion". In this regard, the apparatus, system, and method of this disclosure may find application in physical security situations to detect living beings through a visually opaque wall, for example.

Information about respiration can be acquired in the following way. Firstly, the frequency of respiration is a useful means of characterising breathing patterns as faster breathing is associated with respiratory distress (for example). Respiratory frequency can be defined as the number of breaths per minute, e.g., 10 breaths per minute. Moreover, variability in the respiratory frequency can be a useful indicator of sleep state. Respiratory frequency is more variable in Rapid-Eye-Movement (REM) than in non-REM sleep. To calculate respiratory frequency, the signal from the respiratory signal (as shown in FIG. 4) is processed. Respiratory frequency is calculated over a certain time scale (e.g., 10 seconds or 100 seconds) by taking the power spectral density estimate of the signal. Conventional techniques for calculating power spectral density such as the averaged periodogram may be used. If sections of the respiratory signal have been excessively corrupted by motion, then a technique called Lomb's periodogram may be used, which can estimate power spectral density with missing sections of data. Once the power spectral density (PSD) has been calculated, the respiratory frequency is located by searching for the peak in the PSD in the range 0.1 to 0.8 Hz (which is the normal range of human breathing frequencies). Since adults typically have lower respiratory frequencies than infants and young children, the search range can be reduced to 0.1 to 0.5 Hz (for example). If the power in the peak exceeds the average power in the rest of the band by a certain amount (e.g., at least 50% stronger than background), then we recognise that frequency as the respiratory frequency for the epoch. In that manner, the respiratory frequency of each epoch can be calculated over the period of measurement.

The amplitude of the respiration signal is also of importance, and is reflected in the amplitude of the sensor respiration signal. Amplitude variation is an identifying feature of a sleep disordered breathing called Cheyne-Stokes respiration, in which the amplitude of breathing varies from very shallow to very large over a time scale of typically 60 seconds. The current invention can reliably estimate the amplitude of the breathing signal over an epoch by taking the square root of the power at and near the peak of the respiratory power spectral density discussed above. In this way, the variation of amplitudes over epochs of time can be tracked.

The periodic nature of the patterns in the respiratory signal are also important as it can indicate the presence of sleep disorder breathing. Obstructive apnea manifests itself as repeated patterns of disrupted breathing and recovery breaths over time scales of typically 60 seconds. The current disclosure can reliably detect these patterns by calculating a power spectral density (PSD) of the epochs of the breathing signal and isolating the frequency component in the 0-0.05 Hz bands.

Obstructive apnea may be detected applying a threshold to these frequency components and where a component exceeds the threshold then it can be said with high reliability that obstructive apnea is present. A more accurate way is to use the frequency component values (or other measures derived from the breathing signal) as an input into a classifier (for example a linear discriminate classifier) which then output the probability of apnea having occurred during the epoch. An estimated Apnoea-Hypopnoea index (AHI) value may be calculated by summing probabilities for each epoch, dividing by the duration of the recording to estimate the minutes per hour in apnea. An AHI value may then be calculated by multiplying the minutes-per-hour in apnoea by a predetermined constant.

In addition to the respiratory information, we can also process the cardiac and movement information to enhance the accuracy of the system in detecting sleep disordered breathing. For example, information from the cardiac activity can be used the enhance the classification accuracy of the respiratory based detector of sleep disordered breathing. Using the pulse of that time's a set of features are calculated for each epic, which consists of a plurality of the following PSD of the pulse event time, the standard deviation of the pulse event times, and the serial correlation of the pulse event times. These cardiac activity features are processed by a classifier (such as a linear discriminate classifier) to produce a probability of apnea. Further, information from the activity can be used to determine when the subject was aroused from sleep by counting the number of movement ethics per epic and processing this with a linear discriminate classifier to produce a probability of apnea so as to identify individual apnoeic events.

The three probabilities (or two or more probabilities if the quality is poor and no features are calculated for one or more of the breathing, cardiac, or movement signals) can be combined using a probability combiner (for example, by averaging the probabilities).

And estimated Apnea-Hypopnoea Index (API) value may be calculated by averaging the combined probabilities for each epic and multiplying by the number of epochs per hour to estimate the minutes per hour in apnea. An AHI value may then be calculated by multiplying the minutes per hour in apnea by a predetermined linear mapping.

The apparatus and system of this disclosure has been trained to estimate the AHI using the respiratory, movement, and heart rate data from 125 subjects who have undergone a full polysomnogram. The results show that the system can distinguish between patients with moderate to severe apnea (AHI>15) from patients free of apnea (AHI<5) with an accuracy of greater than 82%.

It is also of importance to sense when respiration is absent (so called central apnea), for example, in monitoring human babies. This can be measured by taking the respiratory amplitude measure defined above over an epoch of interest, and if it falls below a certain threshold (which determines the sensitivity), then it is said that respiration is absent. For example, if no respiration is present for an epoch of 15 seconds in babies, then an alarm can be sounded to alert the user to the central apnea condition.

Information about cardiac activity may be acquired in the following way. The initial "cardiac signal" is acquired through bandpass filtering of the raw sensor signal, using a bandpass filter. The resulting signal is then called the ballistocardiogram. Each contraction of the heart is associated with a characteristic pulse shape seen at the surface of the skin. Each pulse shape can then be determined using a simple technique such as peak finding, or through a more elaborate template matching approach. In the template matching approach, a template pulse shape (derived from previous recordings) is correlated with the ballistocardiogram. The points at which the correlation is highest are determined to be the pulse event times.

The heart rate can then be determined by counting the number of pulse shapes per unit time. Other useful parameters such as inter-cardiac intervals can be determined by calculating the difference between pulse shape times. For example, if the pulse shape times are [0.1 s, 1.1 s, 2.3 s, 3.1 s, . . . ] then the corresponding inter-cardiac intervals are given by 1 s, 1.2 s, and 0.8 s.

As well as determining respiration rate and amplitude, cardiac rate, and motion, the system provides for means to combine signals for calculation of further useful outputs. For example, the system can be sued to determine whether a person is asleep or not over a defined epoch of measurement. The means for doing so is as follows.

Data from the respiration, cardiac and motion channels is segmented into epochs of time. For example, an epoch might consist of readings over 5 seconds or over 5 minutes, depending on the desired configuration. For each epoch, a set of features are calculated, which may include one or more of the following conventionally known and determined features: The count of activities; the mean amplitude of activity counts; the variance of activity counts; the dominant respiratory frequency; the respiratory power (e.g., the integral of the PSD in a region about the dominant respiratory frequency); the heart rate; the variability of the heart rate; the spectrum of the respiration signal; and the spectrum of the raw signal.

Selected features may be fed into a classifier model (such as a conventional linear discriminant analysis classifier) which will then provide the probability for that epoch to belong to a certain class of interest. As a specific example, three classes are known and defined in the art for sleep state: AWAKE, NON-REM SLEEP, REM SLEEP. Each of these classes may be associated in a probabilistic sense with a preferred distribution of feature values, and the classifier model uses this statistical fact to provide a classification output for each epoch. Moreover, probabilities from each epoch can be further combined to enhance the accuracy of the classification. These epoch classifications can then be combined over an entire night's recording to provide a so-called hypnogram, which maps the time period into different sleep stages. An important parameter that can be derived from the hypnogram is the sleep efficiency, which is the percentage of time asleep as a fraction of the total time in bed.

The information can also provide a measure of sleep quality by measuring motion over the night's sleep. As above, the data is divided into epochs of time, and activity count features are measured over each epoch. Based on comparison with a previously collected database, and using the classifier methodology outlined above, each epoch can then be classed as "no motion", "gentle motion", "moderate motion" or "severe motion". From these epoch classifications, a sleep quality index can be determined by counting the number of epochs assigned to each motion class.

The apparatus, system, and method of this disclosure can also be used to provide information about the transition between non-REM (rapid eye movement) sleep and REM sleep, as such transitions are known to typically accompanied by positional changes and relatively large movements, after a period of relatively low motion.

Further, the apparatus, system, and method of this disclosure can also be used to provide a respirogram over the night's recording in a much less intrusive and complicated manner than is conventionally available. The respirogram is a measure of respiratory frequency over the night's sleep, and can be calculated by plotting the respiratory frequency over the entire night's recording.

Discussion of Various Embodiments

Various embodiments of an apparatus, system, and method of physiological monitoring are contemplated by this disclosure. In one embodiment, an apparatus useful in detecting, analyzing, and displaying one or more of a respiration parameter, cardiac activity, and bodily function or movement of a subject includes a processor configured to analyze a signal reflected from the subject without physical contact with the subject and to derive measurements of various physiological parameters of the subject, e.g., a human subject. A display may be configured to provide the analyzed and derived measurements to a local or remote user of the apparatus. The reflected signal can be an RF signal, or it may be another type of signal, e.g., ultrasound, infrared, and/or visible light.

In another aspect of this and various embodiments, a sensor may be coupled to the processor and arranged to receive the signal reflected from the subject. The sensor and processor are arranged to operate without any direct or indirect physical contact with the subject. In another aspect of this embodiment, the reflected signal may be generated by a transmitter collocated with the apparatus. Further, the transmitter may be configured to generate an RF energy signal compatible for use with a human subject. In still another aspect of this and various embodiments, a multiplier circuit may be arranged to multiply the reflected signal with a transmitted signal and to output a baseband signal representing respiration, cardiac, and a bodily function or movement therefrom. Bodily functions may include, for example, urination of a child which may be detected by small bodily movements of the subject.

In another aspect of this and various embodiments, the processor may be configured to recognize periods of bodily motion of the human subject by identifying peaks in an energy envelope of the baseband signal. Further, the processor may be configured to recognize periods of bodily motion of the human subject by counting a number of threshold-crossings of the baseband signal per unit time. In another aspect of this and various embodiments, a sensor is provided and the processor is configured to receive the baseband signal and to output a processed signal in response, and the processor may further be configured to use the processed signal to distinguish breathing activity of the human subject or cardiac activity of the human subject. The processed signal may be the output of bandpass, multi bandpass, or signal separation processes implemented by known digital signal processing techniques, for example, by independent component analysis.

In another aspect of this and various embodiments, the processor may be configured to determine an activity count for a measurement epoch by calculating an energy of the baseband signal relative to other epochs. Further, the processor may be configured to run a classifier model so as to determine a Cheyne-Stokes respiration pattern by processing features obtained from a respiratory signal derived from the baseband signal. In addition, the processor may be configured to determine an Apnoea-Hypopnoea Index (AHI) by processing a respiratory signal derived from the baseband signal; the AHI may be determined solely by a derived respiratory effort parameter. In a related aspect of this and various embodiments, the processor may be configured to determine a the sleeping status of the subject by analysis of a motion signal derived from the baseband signal. In other aspects, the classifier model may be run to determine a sleep state by combining one or more of motion signals, breathing signals, and cardiac signals provided by the classifier model. In a further related aspect of this and various embodiments, the processor may be configured to recognize a central apnea condition by determining that breathing and motion activity of the subject are below a predetermined threshold for a period of time. In further aspects, the processor may be configured to recognize a respiratory distress condition of the human subject by comparing a derived respiratory frequency with an existing set of respiratory measurements.

In other aspects of the embodiment, the processor causes a visual or aural indication device to signal one or more of a sleep status, a breathing parameter, a heart rate, or a bodily movement of the subject to a user.

In another embodiment, a system for measuring, analyzing, and displaying one or more of a respiration parameter, cardiac activity, and bodily movement or function of a subject includes, inter alia, a transmitter arrangement configured to propagate a radio frequency signal toward the subject and a receiver arranged to receive the signal reflected from the subject. A processor is arranged to analyze the reflected signal to produce measurements of one or more of a respiration parameter, cardiac activity, and a bodily movement or function. A monitor may be used to provide selected information to a local or remote user of the system by either an audible or visual indication, or both. The system may further include one or more auxiliary sensors coupled to the processor, e.g., one or more of an acoustic sensor, temperature sensor, humidity sensor, and a light sensor.

In another embodiment, a method for measuring, analyzing, and displaying one or more physiological parameters of a subject includes, among other steps, sensing a signal reflected from the subject and processing and analyzing the reflected signal. The reflected signal may be an RF signal. One or more physiological parameters pertaining to the subject are derived. The physiological parameters may include one or more of a respiration parameter, cardiac activity, and bodily movement or function of the subject. Finally, selected derived information may then be made available to the user, for example, on a display monitor. In other aspects, an audible alarm may be sounded in response to a determination that one or more of the physiological parameters is outside a normal limit. Such physiological parameters may include, for example, an Apnoea-Hypopnoea Index (AHI) obtained by analyzing a respiratory signal derived from the reflected radio signal.

In a related embodiment, a computer-readable medium contains computer instructions thereon which, when executed on a computer, carry out the functions of measuring, analyzing, and displaying one or more physiological parameters of a living subject by processing and analyzing a signal reflected from the living subject; deriving said one or more physiological parameters pertaining to said living subject, said one or more physiological parameters comprising one or more of a respiration parameter, cardiac activity, and bodily movement or function of a subject; and making selected derived information available to a user.

In another aspect of this and various embodiments, the reflected signal may be processed and analyzed by using a baseband signal obtained by multiplying a transmitted signal by the reflected signal. The baseband signal may be analyzed with a classifier and an activity count may then be determined in response to the classification result. The determined activity count to determine said one or more physiological parameters.

EXPERIMENTAL RESULTS

One example of the application of the apparatus, system, and method of this disclosure is in the detection and diagnosis of various sleep disorders.

Background: Actimetry is a widely accepted technology for the diagnosis and monitoring of sleep disorders such as insomnia, circadian sleep/wake disturbance, and periodic leg movement. In this study we investigated a sensitive non-contact biomotion sensor to measure actimetry and compare its performance to wrist-actimetry. A data corpus consisting of twenty subjects (ten normals, ten with sleep disorders) was collected in the unconstrained home environment with simultaneous non-contact sensor and ActiWatch® actimetry recordings used as a baseline standard. The aggregated length of the data was 151 hours. The non-contact sensor signal was mapped to actimetry using 30 second epochs and the level of agreement with the ActiWatch® actimetry determined. Across all twenty subjects, the sensitivity and specificity was 79% and 75% respectively. In addition, it was shown that the non-contact sensor can also measure breathing and breathing modulations. The results of this study indicate that the non-contact sensor is a highly convenient alternative to wrist-actimetry as a diagnosis and screening tool for sleep studies. Furthermore, as the non-contact sensor measures breathing modulations, it can additionally be used to screen for respiratory disturbances in sleep caused by sleep apnea and chronic obstructive pulmonary disease (COPD).

Sleep assessment can be based on many different types of signals. Existing methods to measure these signals, include polysomnography (PSG), actigraphy, and sleep diaries. PSG, the "gold standard" for sleep assessment, may be impractical for some applications, particularly for usage in the home. It can be both intrusive and expensive.

Actimetry is a mature technology, developed over the last 25 years. An actimeter is a wearable motion sensing and data logging device that records the motion data continuously for days, weeks, or even longer. The actimetry monitor is generally placed on the non-dominant wrist, leg, or sometimes the trunk. The digitized actimetry signal can be processed on a computer and used to diagnose and monitor sleep disorders such as insomnia, circadian sleep/wake disturbance, and periodic leg movement (PLM). Actigraphy is not considered to be as reliable as full PSG studies for the diagnosis of sleep disorders, but due to suitability to record continuously for long periods of time, its convenience and its low-cost, it is a very useful screening device. It is considered more reliable than patient sleep logs.

A brief description of conventional actimetry technology is given here. A sensitive linear accelerometer is employed to capture movements. The movement is bandpass filtered (typically 0.25 to 2-3 Hz). This eliminates very slow movements and fast human movements such as shivers and involuntary tremors. Voluntary human movements rarely exceed 3-4 Hz.

The motion is transduced into an analog electrical signal and digitized. The movement counts are accumulated over an epoch, the length of which is generally user programmable. The analog signal can be digitized using three methods, a) time above a threshold, b) number of zero crossings, or c) digital integration. The time above threshold method accumulates the amount of time the analog signal is above a pre-determined threshold during the epoch. An example threshold might be 0.2 g (g=9.8 m/s2). Two issues with this method are, (a) that there is a saturation effect because the signal amplitude above the threshold is ignored and, (b) movement acceleration is not measured.

The zero crossings method counts the number of times that the actimetry signal level crosses the zero line during an epoch. Three issues with this method are that, (a) movement amplitude is not captured, (b) movement acceleration is not measured, and, (c) it is susceptible to large invalid count readings due to high frequency artifacts. The digital integration method samples the analog actimetry signal at a high rate. The area under the curve is then calculated. Both amplitude and acceleration information is captured. The digital integration method has been found to outperform the time above threshold and zero crossing methods for identifying movement.

Actigraphy is often reported as counts but it is important to stress that different hardware devices and different actimetry algorithms can produce very different counts for the same actimetry. Thus, a direct comparison between ActiWatch® actigraphy and actimetry derived from the non-contact sensor is difficult. An alternative method is to compare the temporal location of actimetry. This would allow the capture of false positives and false negatives.

Non-contact radar technology sensors can monitor respiratory, movement, and even cardiac signals in an un-intrusive manner. Non-contact sensors offer a number of advantages over existing technologies in that 1) there is no contact with the subject, 2) the cost of the sensor is very low, and 3) the sensors are very portable.

Method: Simultaneous actimetry and non-contact sensor recordings were recorded for twenty subjects consisting of twelve females and eight males, with a mean age of 46.7 years (SD 21.3). Nine of the subjects were classified as healthy. For the other eleven subjects, six had severe sleep apnea, two had moderate sleep apnea, one had COPD, one had childhood obesity, and one suffered from insomnia. The recordings were made in the unconstrained home environment under a doctor's supervision.

TABLE I

DETAILS OF THE SUBJECTS IN THE TEST CORPUS

| Record Number | Age (years) | Sex | Health Status | Length (hours) |
|---|---|---|---|---|
| 1 | 36 | F | Healthy | 8.04 |
| 2 | 29 | F | Healthy | 8.33 |
| 3 | 67 | F | Moderate Sleep Apnea | 7.67 |
| 4 | 30 | F | Healthy | 4.38 |
| 5 | 49 | M | Healthy | 6.89 |
| 6 | 30 | F | Healthy | 7.36 |
| 7 | 31 | F | Healthy | 6.11 |
| 8 | 79 | F | COPD | 7.53 |
| 9 | 8 | F | Childhood Obesity | 8.06 |
| 10 | 23 | F | Healthy | 8.84 |
| 11 | 34 | F | Healthy | 8.74 |
| 12 | 30 | F | Healthy | 7.56 |
| 13 | 34 | M | Moderate Sleep Apnea | 6.33 |
| 14 | 69 | M | Severe Sleep Apnea | 6.72 |
| 15 | 79 | F | Insomnia | 8.19 |
| 16 | 58 | M | Severe Sleep Apnea | 8.02 |
| 17 | 49 | M | Severe Sleep Apnea | 8.16 |
| 18 | 51 | M | Severe Sleep Apnea | 7.82 |
| 19 | 77 | M | Severe Sleep Apnea | 7.92 |
| 20 | 72 | M | Severe Sleep Apnea | 7.97 |

Actimeter (ActiWatch®): The Actiwatch® (registered trademark of Mini Mitter Company) is a long-term activity monitoring device used in this study to provide a baseline of activity counts. It is cordless, and data is transferred to the PC via a close proximity RF link. The Actiwatch® contains a sensor capable of detecting acceleration in two planes. It is sensitive to 0.01 g, and integrates the degree and speed of motion and produces an electrical current with varying magnitude. An increased degree of speed and motion produces an increase in voltage. The watch converts this signal and stores it as activity counts. The maximum sampling rate is 32 Hz. For this study, the watch was placed on the non-dominant wrist and set to record the number of activity counts during 15 second intervals (epochs).

Non-contact Sensor: The non-contact sensor employed in this study is a multi-channel biomotion sensor employing 5.8 GHz Doppler radar using a modulation system that limits both the maximum and minimum range. Quadrature operation eliminates range-dependent sensing nulls. The baseband inphase (I) and quadrature (Q) signals were filtered using analog active filters with bandwidths (0.05-1.6) Hz and (1-5) Hz. The emitted power is very low-less than 10 mW.

Non-contact Sensor Data Logger: The design of the non-contact biomotion logger used in this study shares some of the benefits of existing actimeters including convenience of use, light weight, portability, cheap, low power usage, non-intrusive, and the capacity to record for several days or even for weeks. The data logger manufactured by BiancaMed Ltd. incorporates all of the aforementioned characteristics, and it can be powered by the electric mains or battery. It is a standalone device which records data from an internal non-contact sensor to an SD flash card for easy transfer to a PC for analysis. It is capable of logging continuously for weeks with standard off-the-shelf SD cards (up to 4 GB), as used in digital cameras. It contains an independent battery-powered clock which tags the movement data with accurate time information and digitizes the sensor channels at 50 Hz with 10-bit resolution. The user places the data logger no more than 1 meter from the bed, between 0.25 to 0.5 meters above the height of the mattress, and facing towards the torso of the subject. For the detection of movement (actimetry), positioning of the logger has been found not to be crucial. For detection of breathing, the data logger is more sensitive to positioning however, experiments show that if placed within the above limits, good signals are obtained.

Non-contact to Actimetry Mapping: The I and Q channels were combined when doing breathing analysis, however, for actimetry data, it is sufficient to use only one channel (either I or Q). The mapping from the non-contact sensor to actimetry is carried out as follows:

1) The first stage is a digital band pass filter with passband (1.5, 4.6) Hz, stopband (0.7, 4.9) Hz, 3 dB passband, and stopband attenuation of 50 dB; implemented as a 7th order Butterworth filter. This filter attenuates the breathing frequencies, thus emphasizing the movement frequencies.
2) The respiration signal is then removed with a sort filter.
3) Finally, the signal is thresholded and summed into non-overlapping two second bins to give an actimetry count. The two second epochs can then be downsampled to the appropriate epoch and compared with wrist based actimetry.

Due to varying clock offsets between the ActiWatch® and data logger, the actimetry and non-contact sensor recordings were aligned manually. After alignment, the signals were truncated so that only data that were recorded simultaneously were retained. The length of each aligned and truncated set of recordings is given in Table 1. The average length is 7.53 hours with an aggregated length of 151 hours across all 20 recordings.

Performance Measure: The performances measures are epoch based. The actimetry counts were aggregated into 30 second epochs for both the ActiWatch® and the non-contact actimetry. For each epoch, counts greater than one were quantized to one and a comparison made between the quantized counts of the ActiWatch® and the non-contact sensor, i.e., the comparison measures the accuracy of temporal activity location, rather than magnitude of the actimetry. Table 2 shows the four possible states that can arise when comparing the reference epoch (ActiWatch® actimetry) with the non-contact actimetry epoch, TN, FN, FP, and TP refer to true negative, false negative, false positive, and true positive, respectively. The sensitivity (the probability that an epoch with actimetry is detected by the non-contact actimetry mapping) is defined as:

$$\text{Sensitivity} = \frac{TP}{TP + FN},$$

and the specificity (the probability that the an epoch without actimetry is labeled the same by the non-contact actimetry mapping) is defined as:

$$\text{Specificity} = \frac{TN}{TN + FP}.$$

TABLE II

THE FOUR POSSIBLE COMPARATIVE STATES THAT CAN ARISE BETWEEN ACTIWATCH ® ACTIMETRY AND NON-CONTACT ACTIMETRY, BASED ON QUANTIZED EPOCH ACTIMETRY COUNTS

| | | Non-contact Actimetry | |
|---|---|---|---|
| | | 0 | 1 |
| ActiWatch ® Actimetry | 0 | TN | FP |
| | 1 | FN | TP |

Figure 14:
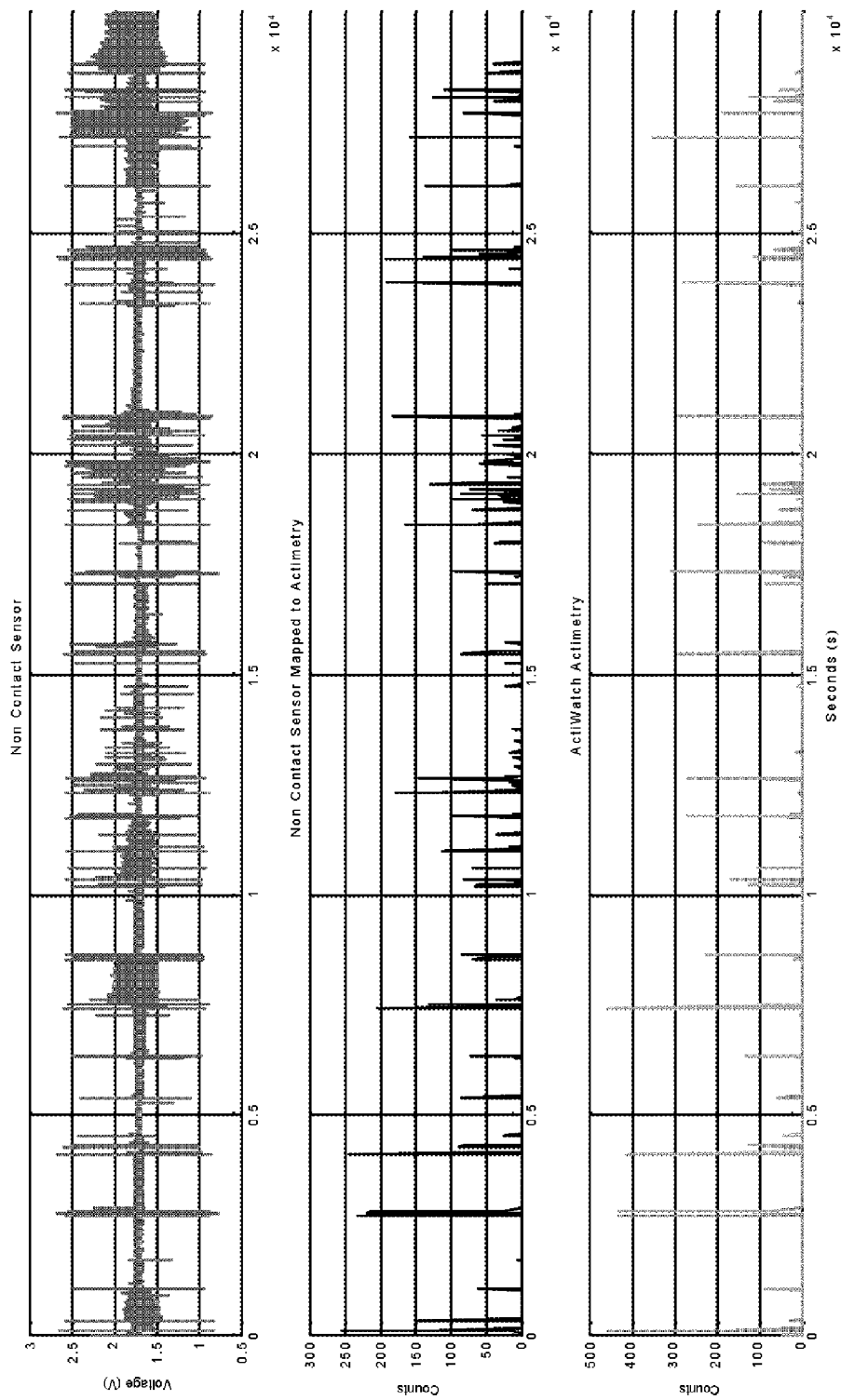
FIG. 14 provides a non-contact sensor recording for Record Number 2 (top axis) with the actimetry recording on the bottom axis in which the signals have been aligned and truncated, and in which the middle axis shows the non-contact signal mapped to actimetry.

Results: FIG. 14 provides experimental results from a non-contact sensor recording for Record Number 2 (top axis) with the actimetry recording on the bottom axis in which the signals have been aligned and truncated, and in which the middle axis shows the non-contact signal mapped to ActiWatch® actimetry. From FIG. 14, it can be seen that the non-contact and ActiWatch® actimetry agree very well in temporal location and also in magnitude. Table III gives the sensitivity and specificity for each of the twenty comparisons of the noncontact with ActiWatch® actimetry.

TABLE III

EPOCH BASED PERFORMANCE MEASURES FOR EACH OF THE RECORDINGS

| Record Number | TP | FN | FP | TN | Sen (%) | Spec (%) |
|---|---|---|---|---|---|---|
| 1 | 64 | 13 | 107 | 783 | 83 | 88 |
| 2 | 54 | 35 | 68 | 845 | 61 | 93 |
| 3 | 94 | 34 | 329 | 465 | 73 | 59 |
| 4 | 47 | 3 | 81 | 396 | 94 | 83 |
| 5 | 75 | 16 | 26 | 711 | 82 | 96 |
| 6 | 18 | 37 | 32 | 798 | 33 | 96 |
| 7 | 97 | 73 | 59 | 506 | 57 | 90 |
| 8 | 191 | 67 | 97 | 550 | 74 | 85 |
| 9 | 85 | 18 | 136 | 729 | 83 | 84 |
| 10 | 150 | 5 | 152 | 755 | 97 | 83 |
| 11 | 106 | 13 | 528 | 404 | 89 | 43 |
| 12 | 33 | 7 | 26 | 842 | 83 | 97 |
| 13 | 35 | 6 | 361 | 360 | 85 | 50 |
| 14 | 59 | 15 | 71 | 663 | 80 | 90 |
| 15 | 408 | 54 | 431 | 91 | 88 | 17 |
| 16 | 43 | 5 | 72 | 844 | 90 | 92 |
| 17 | 87 | 20 | 229 | 645 | 81 | 74 |
| 18 | 155 | 46 | 384 | 355 | 77 | 48 |
| 19 | 179 | 38 | 265 | 470 | 82 | 64 |
| 20 | 208 | 8 | 284 | 458 | 96 | 62 |
| Mean | 109 | 26 | 187 | 584 | 79 | 75 |

Discussion: Across all twenty subjects, the sensitivity and specificity were 79% and 75% respectively. The non-contact sensor monitors motion over all of the body will thus registers more motion than a single non-dominant wrist positioned ActiWatch®. This may explain the lower specificity value. The sensor also proved to be very reliable, convenient and non-invasive. There were no signal quality or equipment set up issues. None of the subjects reported being disturbed by the sensor. The results of this study show that the non-contact sensor can reliably quantify actimetry. Thus, established actimetry based sleep algorithms can be deployed on non-contact based actimetry data and, for example, sleep efficiency can be estimated. A full PSG was not carried out for this study, and hence expert annotated EEG based sleep staging was not possible.

Due to the lack of expert sleep staging, the sleep efficiencies from the Actiwatch® and non-contact-actimetry were not compared at this time. Our results demonstrate that the non-contact sensor can reliably measure the breathing signal, for example, a spectrogram (not shown) of an overnight non-contact sensor signal and the breathing frequencies of approximately 0.3 Hz (18 breaths per minute) were readily ascertainable. Additionally, a sample non-contact breathing signal taken from a subject with mild sleep apnea provides evidence in the modulations in the breathing signal that apnea is present, and this shows that the apparatus, system, and method of this disclosure, can not only be used as an actimeter, but also can be employed to automatically screen for respiratory disturbances during sleep such as occurs during sleep apnea and COPD.

Conclusion: Thus, it has been demonstrated in one example application that non-contact based actigraphy can capture equivalent information to that of conventional wrist based actigraphy. Furthermore, the non-contact biomotion sensor is a richer source of physiological information. Actigraphy is a single modality signal, whereas, the non-contact biomotion sensor can capture both actigraphy and respiration information. The non-contact sensor also proved to be highly convenient and unobtrusive. Even though this demonstration was conducted using an RF signal, other signal types may be used, e.g., ultrasound, infrared, or visible light.

STATEMENT OF INDUSTRIAL APPLICABILITY

The apparatus, system and method of this disclosure finds utility in non-invasive, non-contact monitoring and analysis of physiological signs of humans or other living subjects such as respiration and cardiac activity. This disclosure also has applications to sleep monitoring, stress monitoring, health monitoring, intruder detection, and physical security.

What we claim is:

1. An apparatus useful in detecting and analyzing one or more of respiration, cardiac activity, and bodily function or movement of a living subject, the apparatus comprising:
a multiplier circuit arranged to multiply a reflected signal with a transmitted pulsed signal and to output a baseband signal representing one or more of respiration, cardiac, and bodily function or movement;
a processor configured to analyze the baseband signal, determine a phase difference between the signal reflected from the subject and the pulsed signal transmitted towards the subject, and derive measurements of said one or more of respiration, cardiac activity, and bodily function or movement from the phase difference; and
wherein the processor is configured to run a classifier model to determine sleep disorder parameters by combining one or more of bodily function or movement, respiration, and cardiac activity.

2. The apparatus of claim 1, further comprising a sensor coupled to the processor and arranged to receive the signal reflected from the subject.

3. The apparatus of claim 1, wherein the reflected signal is associated with a transmitter collocated with the apparatus.

4. The apparatus of claim 3, wherein the transmitter is configured to generate an radio-frequency (RF) energy signal compatible for use with the living subject.

5. The apparatus of claim 1, wherein the processor is configured to recognize periods of bodily motion of the subject by identifying peaks in an energy envelope of the baseband signal.

6. The apparatus of claim 1, wherein the processor is configured to recognize periods of bodily motion of the subject by counting a number of threshold-crossings of the baseband signal per unit time.

7. The apparatus of claim 1, further comprising a sensor and wherein the processor is configured to receive the baseband signal and to output a processed signal in response to a signal received from the sensor, wherein the processor is further configured to use the processed signal to distinguish breathing activity of the subject.

8. The apparatus of claim 1, further comprising a sensor and wherein the processor is configured to receive an output of the sensor and to output a processed signal in response thereto, wherein the processor is further configured to use the processed signal to distinguish a cardiac activity of the subject.

9. The apparatus of claim 1, wherein the processor is configured to determine an activity count for a measurement epoch by calculating an energy of the baseband signal relative to other epochs.

10. The apparatus of claim 1, wherein the classifier model determines a Cheyne-Stokes respiration pattern by processing features obtained from a respiratory signal derived from the baseband signal.

11. The apparatus of claim 1, wherein the processor is configured to determine an Apnea Hypopnoea Index (AHI) by processing a respiratory signal derived from the baseband signal.

12. The apparatus of claim 11, wherein the AHI is determined solely by a derived respiratory effort parameter.

13. The apparatus of claim 1, wherein the processor is configured to determine a sleeping status of the subject by analysis of a motion signal derived from the baseband signal.

14. The apparatus of claim 1, wherein the classifier model determines a sleep state by combining one or more of motion signals, breathing signals, and cardiac signals.

15. The apparatus of claim 1, wherein the processor is configured to recognize a central apnea condition by determining that breathing and motion activity of the subject are below a predetermined threshold for a period of time.

16. The apparatus of claim 1, wherein the processor is configured to recognize a respiratory distress condition of the subject by comparing a derived respiratory frequency with an existing set of respiratory measurements.

17. The apparatus of claim 1, further comprising a visual indication device by which a sleep status of the subject determined by the processor is signaled to a local or remote user.

18. The apparatus of claim 1, further comprising a visual indication device by which a breathing parameter of the subject determined by the processor is signaled to a local or remote user.

19. The apparatus of claim 1, further comprising a visual indication device by which a bodily movement of the subject determined by the processor is signaled to a local or remote user.

20. The apparatus of claim 1, further comprising a visual indication device by which a heart rate of the subject determined by the processor is signaled to a local or remote user.

21. The apparatus of claim 1, wherein the signal reflected from the subject comprises a radio-frequency (RF) signal.

22. A system for measuring and analyzing one or more of a respiration parameter, cardiac activity, and bodily movement or function of a living subject, the system comprising:
a transmitter arrangement configured to propagate a pulsed radio frequency (RF) signal toward the subject;
a receiver arranged to receive an RF signal reflected from the subject;
a multiplier circuit arranged to multiply the pulsed RF signal and the reflected RF signal and to determine a phase difference between the propagated pulsed RF signal and the reflected RF signal;
a processor arranged to analyze the phase difference to produce measurements of one or more of a respiration parameter, cardiac activity, and a bodily movement or function, and
wherein the processor is configured to run a classifier model to determine sleep disorder parameters by combining the measurements of one or more of bodily movement or function, the respiration parameter, and cardiac activity.

23. The system of claim 22, further comprising at least one auxiliary sensor coupled to the processor.

24. The system of claim 23, wherein said at least one auxiliary sensor comprises one or more of an acoustic sensor, temperature sensor, humidity sensor, and a light sensor.

25. A method for measuring and analyzing one or more physiological parameters of a living subject, the method comprising:
- sensing a signal reflected from the living subject;
- multiplying the reflected signal with a transmitted pulsed signal to produce a baseband signal representing one or more of respiration, cardiac, and bodily function or movement;
- processing and analyzing the reflected baseband signal by determining a phase difference between the transmitted pulsed signal and the signal reflected from the living subject;
- deriving, using a processor, the one or more physiological parameters pertaining to the living subject using the phase difference, said one or more physiological parameters comprising one or more of a respiration parameter, cardiac activity, and bodily movement or function of the subject; and
- wherein the processor is configured to run a classifier model to determine sleep disorder parameters by combining the measurements of one or more of the physiological parameters.

26. The method of claim 25, further comprising the step displaying the one or more derived physiological parameters.

27. The method of claim 25, further comprising sounding an audible alarm in response to a determination that one or more of said one or more physiological parameters is outside a normal limit.

28. The method of claim 25, wherein said physiological parameters comprise an Apnoea-Hypopnoea Index (AHI) obtained by analyzing a respiratory signal derived from the reflected signal.

29. The method of claim 25, further comprising the classifier model determining an activity count.

30. The method of claim 29, further comprising using the determined activity count to determine said one or more physiological parameters.

31. The method of claim 25, wherein said step of sensing comprises sensing a radio-frequency (RF) signal.

32. A non-transitory computer-readable medium containing computer instructions thereon which, when executed on a computer, carry out the functions of measuring and analyzing one or more physiological parameter of a living subject by:
- multiplying a signal reflected from a living subject and a pulsed signal transmitted towards the living subject to produce a baseband signal representing one or more of respiration, cardiac, and bodily function or movement;
- processing and analyzing the baseband signal by determining a phase difference between the reflected signal and the pulsed signal;
- deriving said one or more physiological parameters pertaining to the living subject using the phase difference, said one or more physiological parameters comprising one or more of a respiration parameter, cardiac activity, and bodily movement or function of the subject; and
- running a classifier model to determine sleep disorder parameters by combining the measurements of one or more of the physiological parameters.

33. An apparatus useful in detecting and analyzing one or more of respiration, cardiac activity, and bodily function or movement of a living subject, the apparatus comprising:
- a multiplier circuit arranged to multiply a reflected signal with a transmitted pulse signal and to output a baseband signal representing one or more of respiration, cardiac, and bodily function or movement;
- a processor configured to analyze the baseband signal and to derive measurements of said one or more of respiration, cardiac activity, and bodily function or movement therefrom, wherein said processor determines a phase difference between the transmitted pulsed signal and said signal reflected from the subject to derive one or more of said measurements; and
- wherein the processor is configured to run a classifier model to determine sleep disorder parameters by combining one or more of bodily function or movement, respiration, and cardiac activity.

* * * * *